(12) United States Patent
Venkatragavan et al.

(10) Patent No.: US 11,945,788 B2
(45) Date of Patent: Apr. 2, 2024

(54) PROCESS FOR PREPARING PITOLISANT HYDROCHLORIDE AND SOLID-STATE FORMS THEREOF

(71) Applicant: Nuray Chemicals Private Limited, Tamilnadu (IN)

(72) Inventors: Ramasamy Venkatragavan, Thiruvallur (IN); Erugu Balaiah, Thiruvallur (IN); Paramanandam Senthilkumaran, Thiruvallur (IN); Guttha Jayaprasad, Thiruvallur (IN); Manniyam Kailasam Selvam, Thiruvallur (IN); Noti Krishnareddy, Thiruvallur (IN); Sorakka Pichandi Parthipan, Thiruvallur (IN); Murugan Arunkumar, Thiruvallur (IN); Palaniswamy Premkumar, Thiruvallur (IN); Salamuthu Kaliraj, Thiruvallur (IN); Shanmugam Arumugam, Thiruvallur (IN); Singavarapu Ajay Madhukar, Thiruvallur (IN); Raman Silambarasan, Thiruvallur (IN); Saminathan Karthick, Thiruvallur (IN); Kudumudi Jayaraman Parthiban, Thiruvallur (IN); Ravi Silambarasan, Thiruvallur (IN)

(73) Assignee: Nuray Chemicals Private Limited, Thiruvallur (IN)

( * ) Notice: Subject to any disclaimer, the term of this patent is extended or adjusted under 35 U.S.C. 154(b) by 0 days.

(21) Appl. No.: 18/174,238

(22) Filed: Feb. 24, 2023

(65) Prior Publication Data
US 2023/0219914 A1    Jul. 13, 2023

Related U.S. Application Data

(63) Continuation-in-part of application No. 17/751,836, filed on May 24, 2022, now Pat. No. 11,623,920.

(30) Foreign Application Priority Data

Jun. 7, 2021  (IN) .............................. 202141025328
Aug. 6, 2021  (IN) .............................. 202141035609
(Continued)

(51) Int. Cl.
C07D 295/088  (2006.01)
C07C 29/149   (2006.01)

(52) U.S. Cl.
CPC ........ *C07D 295/088* (2013.01); *C07C 29/149* (2013.01)

(58) Field of Classification Search
CPC .... C07D 295/088; C07C 29/149; C07C 51/60
See application file for complete search history.

(56) References Cited

U.S. PATENT DOCUMENTS

| | | |
|---|---|---|
| 6,949,527 B2 | 9/2005 | Zhang et al. |
| 7,910,605 B2 | 3/2011 | Schwartz et al. |

(Continued)

FOREIGN PATENT DOCUMENTS

| | | |
|---|---|---|
| EP | 3239138 A1 | 11/2017 |
| WO | 2007/006708 A1 | 1/2007 |
| WO | 2021/023634 A1 | 2/2021 |

OTHER PUBLICATIONS

EFSA Panel et al., Safety of low-substituted hydroxypropyl cellulose (L-HPC) to be used as a food additive in food supplements in tablet form, EFSA Journal (2018) 16(1): 5062 ("EFSA Panel").

(Continued)

*Primary Examiner* — Carlos A Azpuru
(74) *Attorney, Agent, or Firm* — Daniel R. Evans; Merchant & Gould P.C.

(57) ABSTRACT

The present disclosure relates to a process for preparing pitolisant hydrochloride of Formula-(I) and solid-state forms thereof.

(Continued)

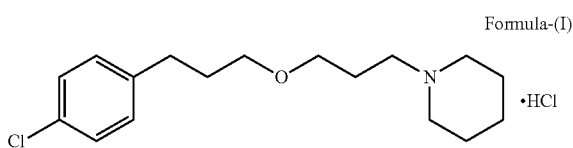

Formula-(I)

27 Claims, 6 Drawing Sheets

(30) Foreign Application Priority Data

Figure 1:
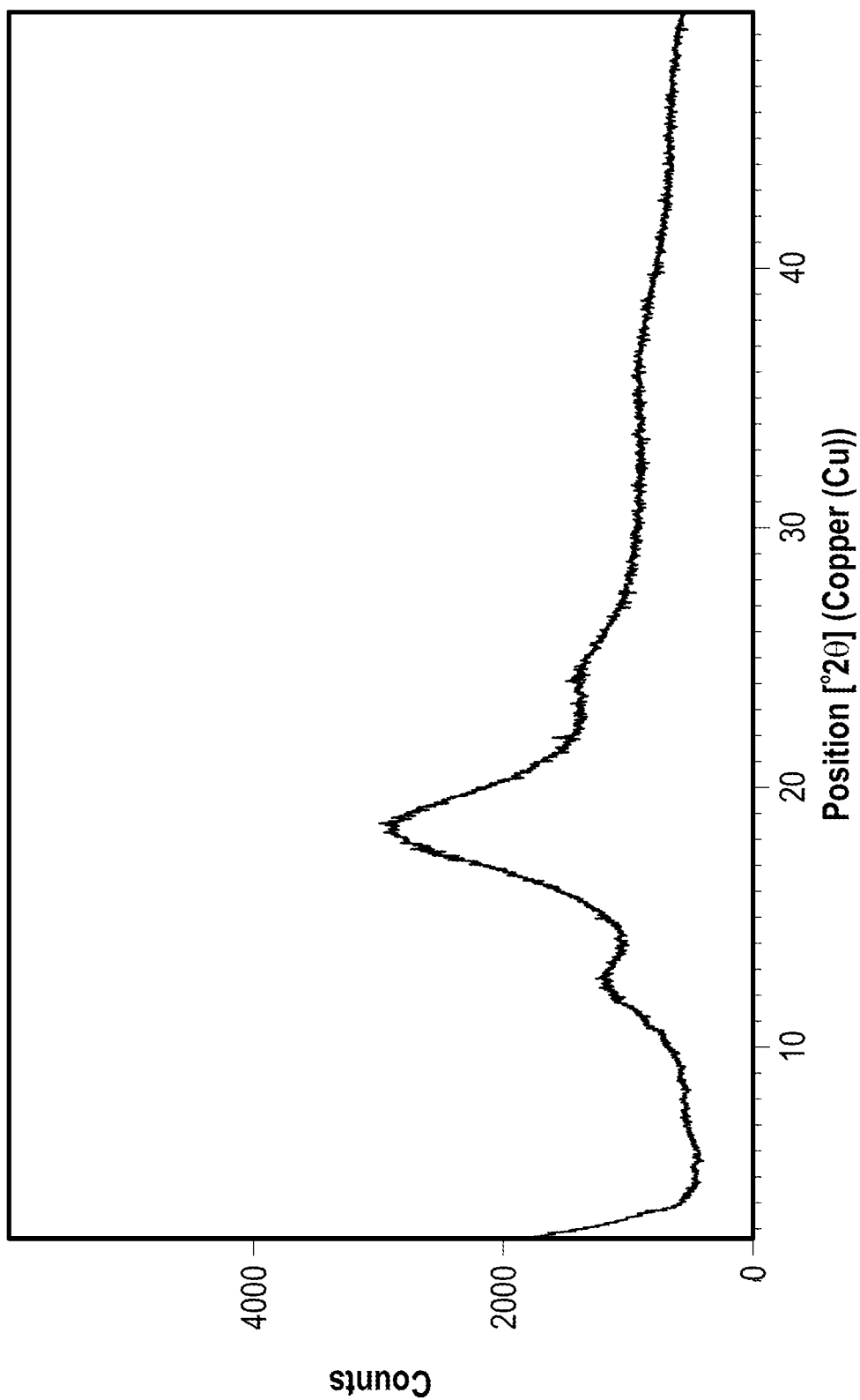

Oct. 13, 2021 (IN) .............................. 202141046743
Feb. 22, 2022 (IN) .............................. 202241009416

(56) References Cited

U.S. PATENT DOCUMENTS

| | | | |
|---|---|---|---|
| 8,207,197 B2 | 6/2012 | Raga et al. | |
| 11,324,692 B2 | 5/2022 | Coello et al. | |
| 2014/0377185 A9 | 12/2014 | Mosher et al. | |
| 2022/0402866 A1* | 12/2022 | Hein | ..................... C07C 211/52 |

OTHER PUBLICATIONS

Greene et al., "Protective Groups in Organic Synthesis" (2nd ed., John Wiley & Sons, Inc.) (1991): 87-118 ("Greene").

Meier et al., "Influence of imidazole replacement in different structural classes of histamine H3-receptor antagonists", European Journal of Pharmaceutical Sciences (2001) 13(3): 249-259 ("Meier").

Sarode et al., "Low-Viscosity Hydropropylcellulose (HPC) Grades SL and SSL: Versatile Pharmaceutical Polymers for Dissolution Enhancement, Controlled Release, and Pharmaceutical Processing", AAPS PharmSciTech (2013) 14(1): 151-159 ("Sarode").

Wakix® (pitolisant) tablets prescribing information, as of Oct. 13, 2020 ("Wakix® Label").

Handbook of Pharmaceutical Excipients, 6th Ed., Eds. Rowe et al. at 314-315, 714-717, (2009) ("Handbook").

* cited by examiner

PROCESS FOR PREPARING PITOLISANT HYDROCHLORIDE AND SOLID-STATE FORMS THEREOF

RELATED APPLICATIONS

This application is a continuation-in-part of U.S. patent application Ser. No. 17/751,836, filed on May 24, 2022, now U.S. Pat. No. 11,623,920, which claims priority to Indian Patent Application Nos. 202141025328, filed on Jun. 7, 2021; 202141035609 filed on Aug. 6, 2021; 202141046743 filed on Oct. 13, 2021; and 202241009416 filed on Feb. 22, 2022.

FIELD OF THE INVENTION

The present disclosure relates to an improved process for preparing pitolisant hydrochloride of Formula-(I) and its solid-state forms thereof.

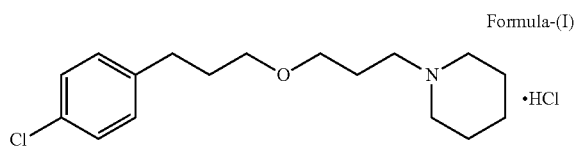 [SMILES: Clc1ccc(CCCOCCCN2CCCCC2)cc1 ; Cl]

Formula-(I)

BACKGROUND

Pitolisant hydrochloride is chemically known as 1-{3-[3-(4-chlorophenyl)propoxy]propyl}piperidine hydrochloride and it is an antagonist/inverse agonist of the histamine-3 (H3) receptor. Pitolisant hydrochloride is approved for the treatment of excessive daytime sleepiness (EDS) in adult patients with narcolepsy. Pitolisant hydrochloride is a white or almost white crystalline powder, and it is soluble in water, ethanol, and methylene chloride and practically insoluble in cyclohexane.

Schwartz discloses a process for preparing pitolisant and its pharmaceutically acceptable salts such as hydrochloride, hydrobromide, hydrogen maleate, and hydrogen oxalate.

Meier discloses a three step process for preparing pitolisant hydrochloride starting with piperidine and 3-chloropropanol, to give the intermediate 3-(piperidin-1-yl)propan-1-ol (2), which is reacted with 3-(4-chlorophenyl)propyl methanesulfonate (3) in the presence of sodium hydride and 15-crown-5 to give pitolisant (1) which is finally reacted with gaseous hydrochloric acid to obtain pitolisant hydrochloride, as shown in Scheme-1.

Scheme-1

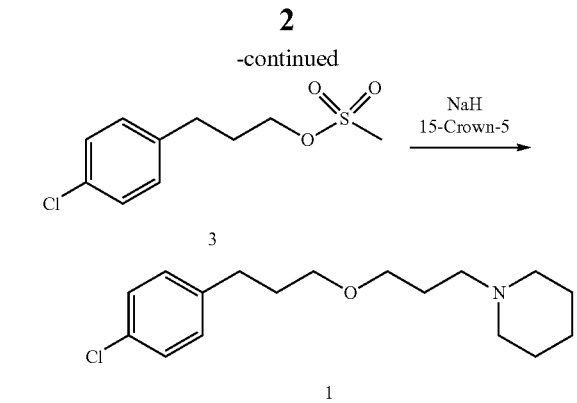

Raga discloses a crystalline form of pitolisant monohydrochloride having a moisture content of 2.7 to 6.5% and its preparation thereof. Raga discloses pitolisant oxalate and pitolisant maleate and their respective solubilities in water. Raga discloses that pitolisant hydrochloride exhibits different properties (e.g., aqueous solubility and stability) when compared to pitolisant oxalate and pitolisant maleate.

Sallarés discloses a process for preparing pitolisant (1) by forming the sodium salt of 3-(piperidin-1-yl)propan-1-ol (2) by reaction with sodium hydride (NaH), and then reacting the sodium salt with 3-(4-chlorophenyl)propyl methanesulfonate (3), as shown in Scheme-2.

Scheme-2

Colombano discloses a process for preparing pitolisant (1) by reacting 4-azaspiro[3.5]nonan-4-ium bromide (4) with 3-(4-chlorophenyl)propan-1-ol (5).

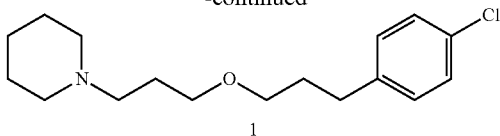

Sefinovic discloses a hydrogen fumarate salt of pitolisant and a process for its preparation.

The prior manufacturing processes for pitolisant utilize sodium hydride (NaH), which is known to be a hazardous and pyrophoric reagent. They have their own handling issues because of its pyrophoric nature and hence these processes are not suitable for a commercial scale.

The reported methods for preparing the compound of Formula-(V) result in the formation of deschloro compound of Formula-(VA) with desired compound of Formula-(V). The deschloro compound having almost same property of compound of Formula-(V), it is cumbersome to remove this impurity from compound of Formula-(V) and its carryover to the next steps results in deschloro impurities selected from deschloro mesyl compound of Formula-(IIIA) and deschloro pitolisant of Formula-(IA). The removal of these impurities is tedious and needs further purification steps.

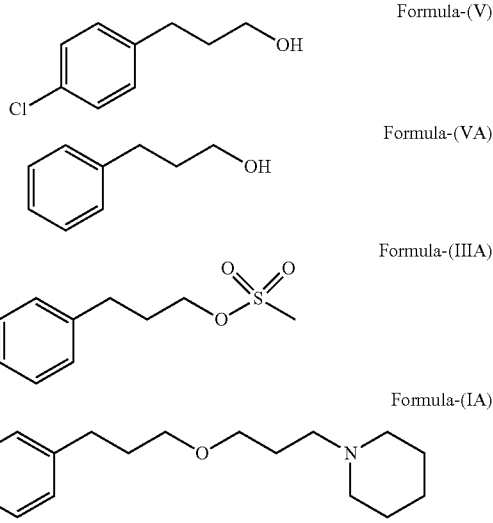

Hence, there is a need for a commercially suitable and non-hazardous process for preparing pitolisant hydrochloride which does not contain deschloro impurities. The following disclosure is the result of an extensive investigation for an improved process for preparing pitolisant hydrochloride using non-hazardous bases, as well as the discovery of novel solid-state forms of pitolisant hydrochloride of Formula-(I).

OBJECTIVES OF THE INVENTION

The main objective of the present disclosure is to provide a non-hazardous process for preparing pitolisant and its pharmaceutically acceptable salts thereof.

Another objective of the present disclosure is to provide new solid-state forms of pitolisant and its pharmaceutically acceptable salts.

Still another objective of the present disclosure is to provide an improved process for preparing 3-(4-chlorophenyl) propanol of Formula-(V), a useful intermediate for preparing chemically pure pitolisant hydrochloride, wherein the pitolisant hydrochloride obtained from this process does not contain deschloro compounds such as deschloro mesyl compound of Formula-(IIIA) and deschloro pitolisant of Formula-(IA).

SUMMARY OF THE INVENTION

Disclosed herein is a process for preparing pitolisant and its pharmaceutically acceptable salts of Formula-(I) comprising:

a) reacting 3-(piperidin-1-yl)propan-1-ol

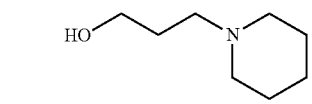

with Formula-(III)

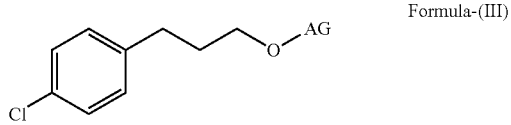

in presence of a base to obtain pitolisant;
b) treating pitolisant with pharmaceutically acceptable salt; and
c) isolating pitolisant pharmaceutically acceptable salt, wherein the base is not sodium hydride.

Also disclosed herein is a process for preparing pitolisant and its pharmaceutically acceptable salts, polymorphs, hydrates, and solid dispersions thereof comprising:

a) providing 3-(4-chlorophenyl)-propionic acid of Formula-(IV);

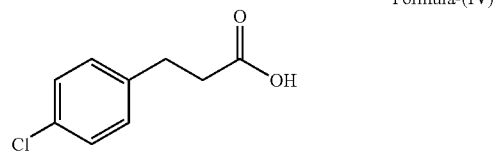

b) converting 3-(4-chlorophenyl)-propionic acid of Formula-(IV) to its acid chloride of Formula-(VI) or acid anhydride Formula-(VIA);

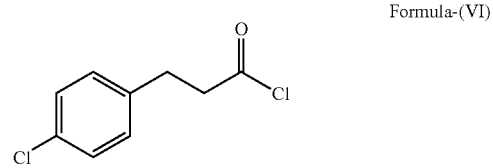 [SMILES: O=C(O)CCc1ccc(Cl)cc1]

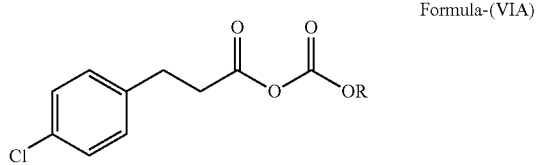

c) reducing acid chloride of Formula-(VI) or acid anhydride Formula-(VIA) to obtain 3-(4-chlorophenyl)-propanol of Formula-(V)

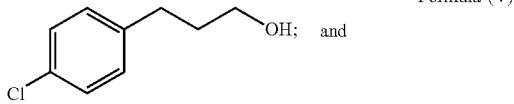

Formula-(V)

and d) converting 3-(4-chlorophenyl)-propanol of Formula-(V) to obtain pitolisant and its pharmaceutically acceptable salts.

The disclosure also relates to a process to obtain a solid-state form of pitolisant hydrochloride of Formula-(I) with or without isolation of crystalline pitolisant hydrochloride of Formula-(I).

DETAILED DESCRIPTION OF THE DRAWINGS

FIG. 1. Powder X-ray Diffraction ("PXRD") pattern of solid dispersion comprising pitolisant hydrochloride and beta-cyclodextrin.

Figure 2:
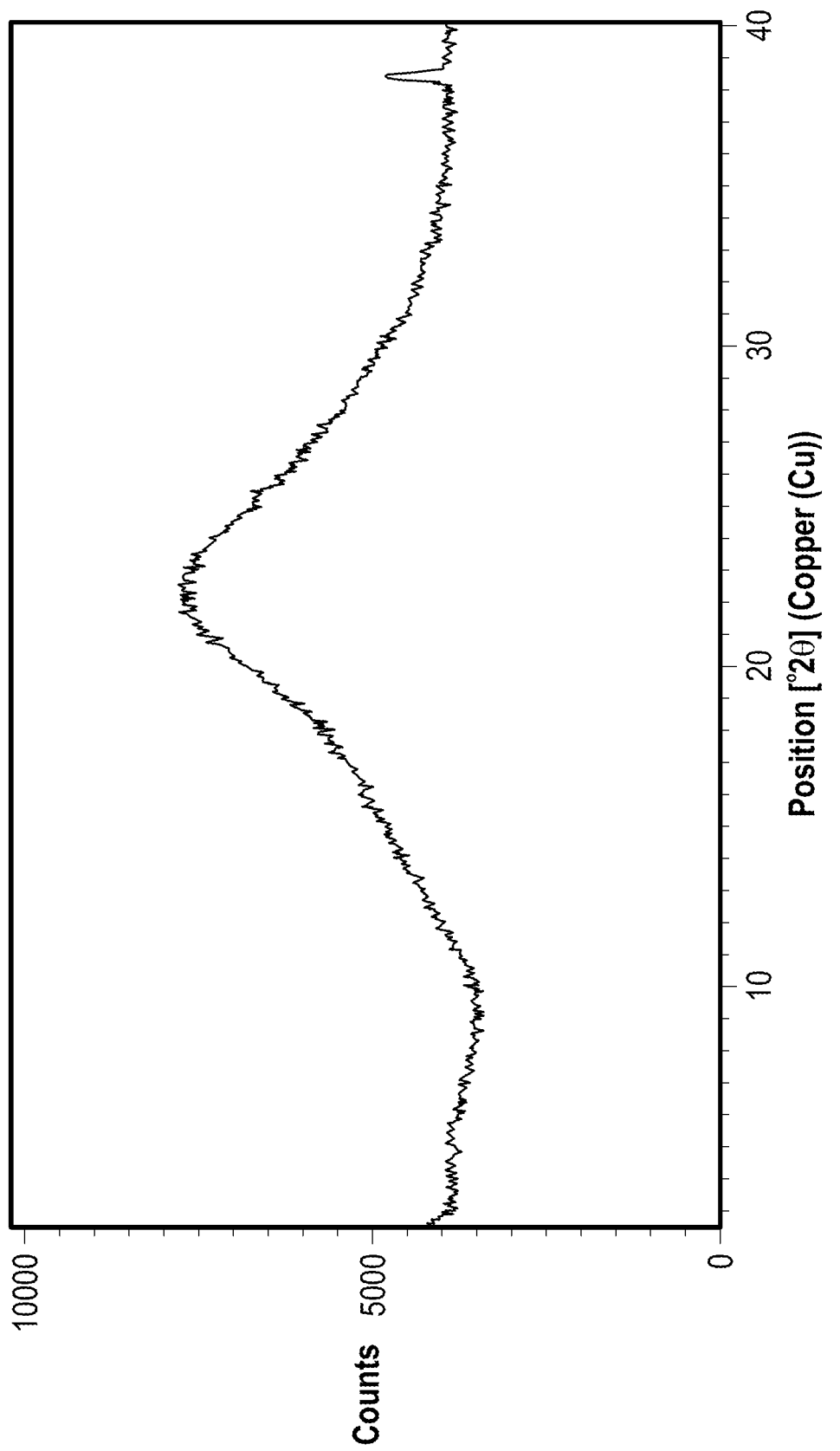

FIG. 2. PXRD of solid dispersion comprising pitolisant hydrochloride and povidone.

Figure 3:
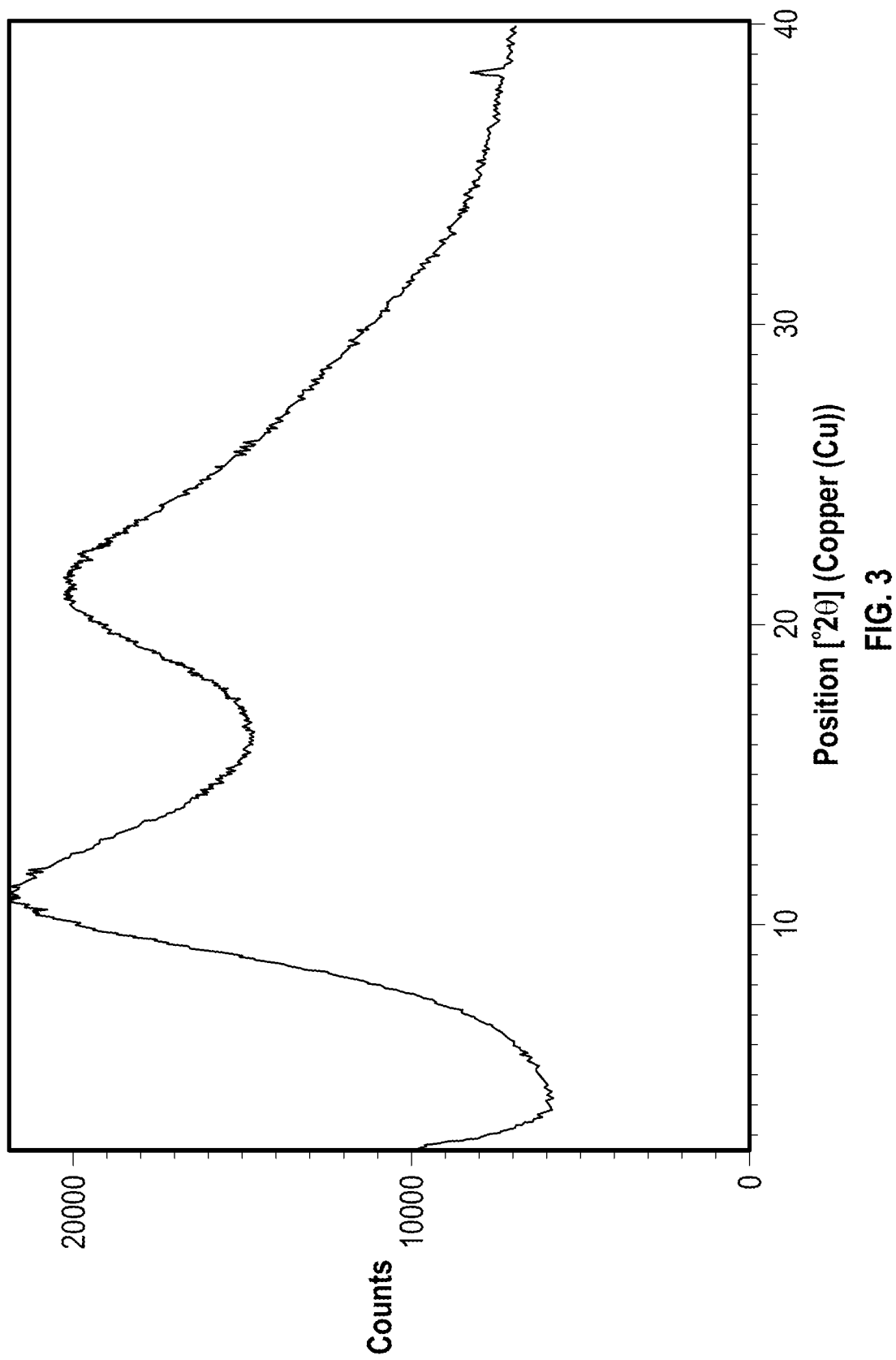

FIG. 3. PXRD of solid dispersion comprising pitolisant hydrochloride and copovidone.

Figure 4:
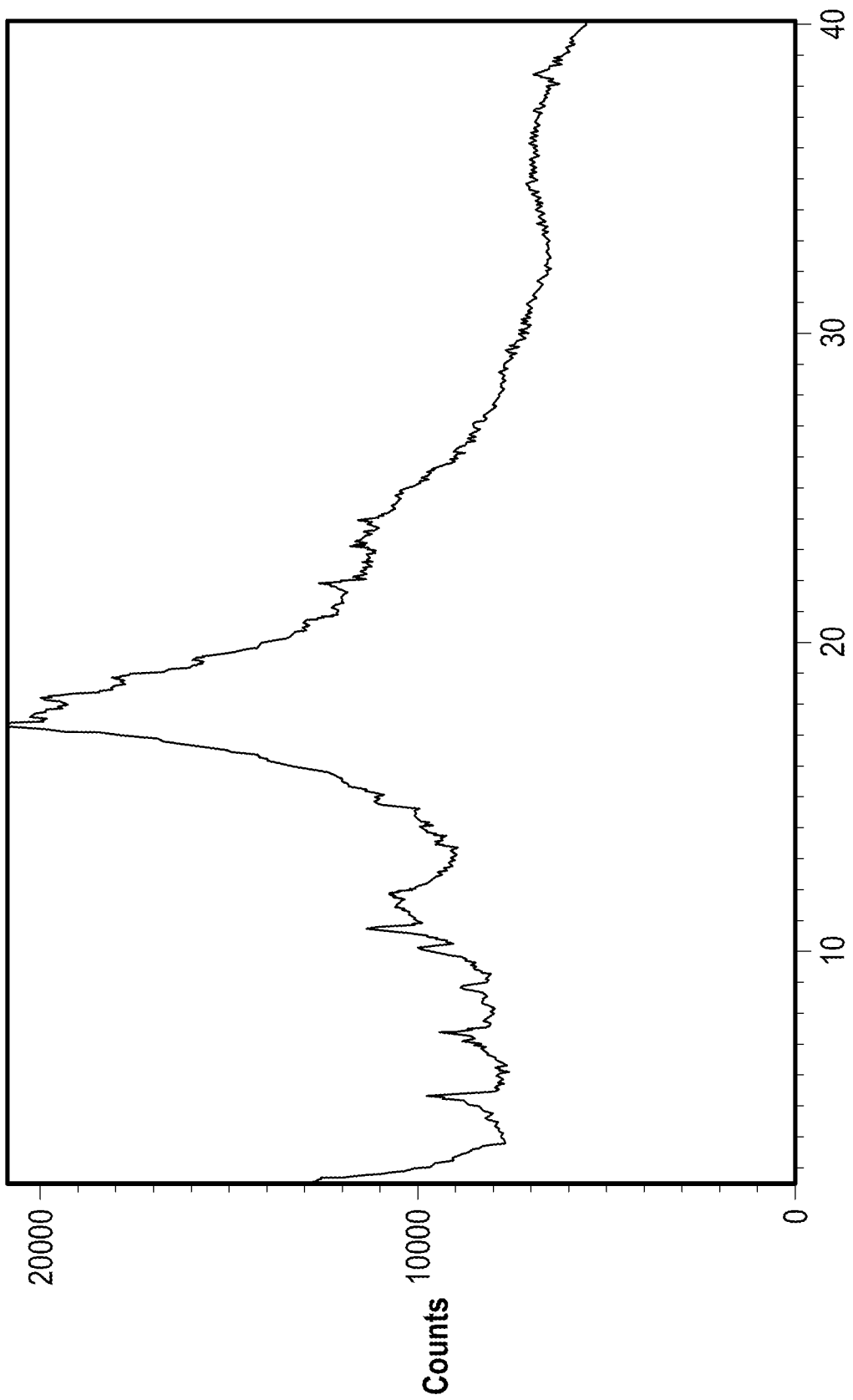

FIG. 4. PXRD of solid dispersion comprising pitolisant hydrochloride sesquihydrate and beta-cyclodextrin.

Figure 5:
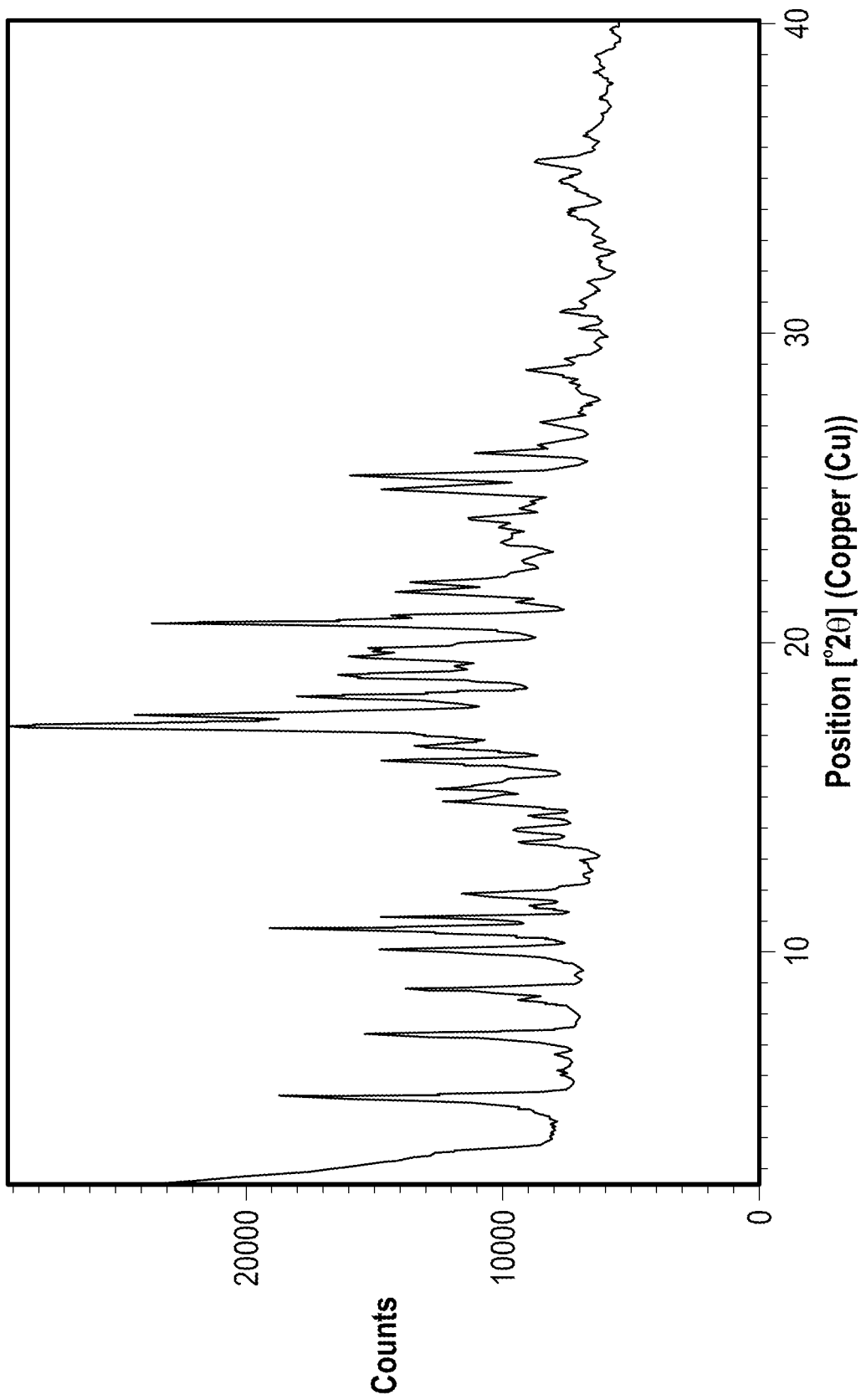

FIG. 5. PXRD of pitolisant hydrochloride sesquihydrate.

Figure 6:
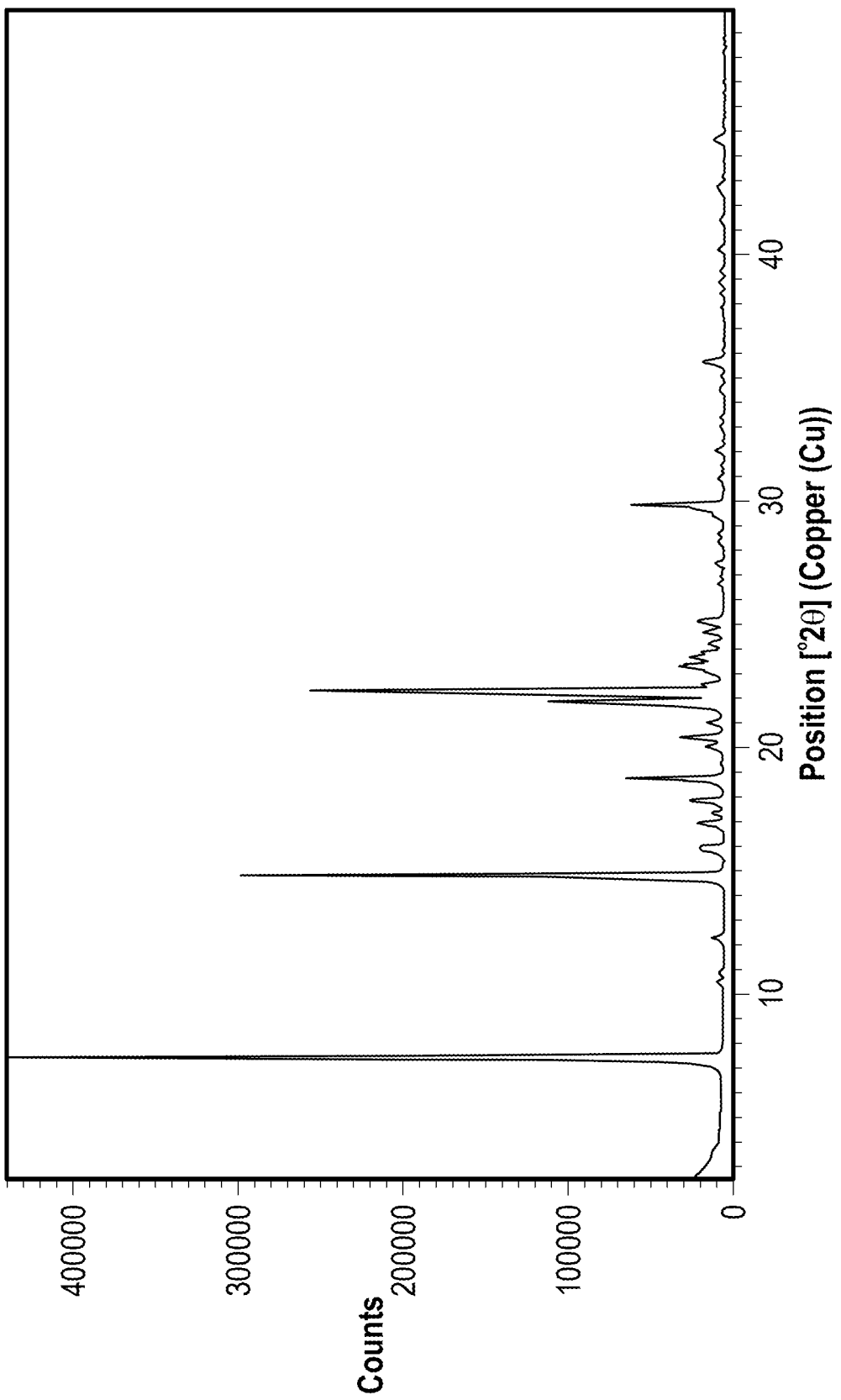

FIG. 6. PXRD of pitolisant oxalate.

DETAILED DESCRIPTION

One embodiment relates to a process for preparing pitolisant and its pharmaceutically acceptable salts comprising:

a) reacting 3-(piperidin-1-yl)propan-1-ol

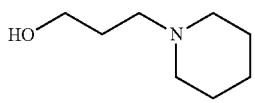

with Formula-(III)

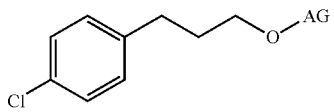

Formula-(III)

in presence of a base to obtain pitolisant;
b) treating pitolisant with pharmaceutically acceptable salt; and
c) isolating pitolisant pharmaceutically acceptable salt, wherein the base is not sodium hydride.

In one aspect, the activating group (AG) may be a suitable electron withdrawing moiety so that the O-AG moiety may undergo a nucleophilic substitution reaction with 3-(piperidin-1-yl)propan-1-ol or a salt thereof.

Examples of activating groups, include, but are not limited to, an alkylsulfonate (e.g., methyl sulfonate, ethylsulfonate), an arylsulfonate (e.g., phenylsulfonate, tolylsulfonate, p-nitrophenyl sulfonate, benzyl sulfonate, etc.), an alkyl ester (e.g., a trifluromethylacyl ester, a trichloromethylacyl ester), an aryl ester (e.g., phenylacyl ester, p-nitro-phenylacyl ester, p-chloro-phenylacyl esters), and the like.

Formula-(III) may be prepared by reacting 3-(4-chlorophenyl)propan-1-ol with a suitable activating group, as reported by, for example, Greene.

In one aspect, Formula-(III) may be selected from 3-(4-chlorophenyl)propyl methanesulfonate, 3-(4-chlorophenyl)propyl ethanesulfonate, 3-(4-chlorophenyl)propyl benzenesulfonate, 3-(4-chlorophenyl)propyl 4-methylbenzenesulfonate, 3-(4-chlorophenyl)propyl 4-nitrobenzenesulfonate, 3-(4-chlorophenyl)propyl 2,2,2-trifluoroacetate, 3-(4-chlorophenyl)propyl 2,2,2-trichloroacetate, 3-(4-chlorophenyl)propyl benzoate, 3-(4-chlorophenyl)propyl 4-nitrobenzoate, and 3-(4-chlorophenyl)propyl 4-chlorobenzoate. In yet another aspect, In another aspect, Formula-(III) may be selected from 3-(4-chlorophenyl)propyl methanesulfonate.

In one aspect, the base used in step a) is organic or inorganic base which is selected from sodium hydroxide, sodium carbonate, sodium bicarbonate, sodium methoxide, potassium hydroxide, potassium carbonate, potassium bicarbonate, potassium tertiary-butoxide, lithium hydroxide, lithium carbonate, lithium bicarbonate, triethylamine, t-butylamine, trimethylamine, N,N-diisopropylamine, and a combination thereof.

In another aspect, the solvent used in step a) comprises aprotic solvent. In yet another aspect, the solvent used in step a) comprises a polar, aprotic solvent.

Suitable solvents (and their boiling points), include, but are not limited to N,N-dimethylformamide (≈153° C.), N,N-dimethylacetamide (≈165° C.), dimethylsulfoxide (≈189° C.), 1-methyl-2-pyrrolidone (≈202° C.), 1-methyl-2-piperidone (≈105-106° C. (12 mmHg), 1,3-dimethyl-2-imidazolidinone (≈225° C.), acetonitrile (≈82° C.), acetone (≈56° C.), dichloromethane (≈40° C.), ethyl acetate (≈77° C.), tetrahydrofuran (≈66° C.), methanol (≈65° C.), ethanol (≈78° C.), isopropanol (≈83° C.), n-butanol (≈118° C.), and a combination thereof.

In another aspect, the solvent used in step a) is selected from N,N-dimethylformamide, N,N-dimethylacetamide, dimethylsulfoxide, 1-methyl-2-pyrrolidone, 1-methyl-2-piperidone, 1,3-dimethyl-2-imidazolidinone, acetonitrile, acetone, dichloromethane, ethyl acetate, tetrahydrofuran, acetone, methanol, and a combination thereof.

In another aspect, the reaction temperature of step a) ranges from about 0° C. to about the reflux temperature of solvent, which may occur at ambient pressure or a reduced pressure (e.g., from about 1 mm Hg to about 320 mm Hg and all values in between).

In another embodiment, the pitolisant hydrochloride solid-state form is selected from a solid dispersion, a co-crystal, a premix, a polymorphic form, and a hydrate thereof.

Yet another embodiment relates to a solid dispersion comprising pitolisant hydrochloride and one or more pharmaceutically acceptable excipients.

In one aspect, one or more pharmaceutically acceptable excipients is selected from a polyvinyl pyrrolidone (viz., povidone, e.g., povidone K-30, povidone K-60, povidone K-90); a polyvinylpyrrolidone vinylacetate (viz., copovidone, e.g., Kollidon VA 64 (K-value of about 25.2 to about 30.8), and Plasdone S 630 (K-value of about 25.4 to about 34.2); a polyvinylacetal diethylaminoacetate (AEA®), a polyvinyl acetate phthalate (PVAP); a polyoxyethylene sorbitan fatty acid ester (viz., polysorbate, e.g., polysorbate 20, polysorbate 40, polysorbate 60, and polysorbate 80); a polyoxyethylene-polyoxypropylene copolymer (viz., poloxamer, e.g., poloxamer 124 (e.g., Pluronic L-55), poloxamer 188 (e.g., Pluronic F-68), poloxamer 237 (e.g., Pluronic F-87), poloxamer 338 (e.g., Pluronic F-108), and poloxamer 407 (e.g., Pluronic F-127)); a polyoxyethylene stearate (e.g., polyoxyethylene (6) stearate, polyoxyethylene (8) stearate, polyoxyethylene (12) stearate, polyoxyethylene (20) stearate, polyoxyethylene (40) stearate, polyoxyethylene (50) stearate, polyoxyethylene (100) stearate); polyethylene glycol monomethyl ether, colloidal silicon dioxide (e.g., Aerosil, Cab-O-Sil, Cab-O-Sil M-5P, Syloid, etc.); a polyethylene glycol (e.g., PEG 200, PEG 300, PEG 400, PEG 600, PEG 900, PEG 1000, PEG 1450, PEG 1540, PEG 2000, PEG 3000, PEG 3350, PEG 4000, PEG 4600, PEG 6000, PEG 8000, etc.); a polyoxylglyceride (e.g., a caprylocaproyl polyoxylglyceride, a lauroyl polyoxylglyceride (e.g., Gelucire 44/14), linoleoyl polyoxylglyceride, oleoyl polyoxylglyceride, and stearoyl polyoxylglyceride); a methylcellulose, a methacrylic acid copolymer (e.g., Eudragit or Eudragit-RLPO); hydroxypropylmethyl cellulose (HPMC); a hydroxypropyl cellulose (HPC); a hydroxypropylmethyl cellulose phthalate; a hydroxypropylmethyl cellulose acetate succinate (HPMC-AS); a hydroxypropylmethyl cellulose; a hydroxypropyl cellulose SSL (HPC-SSL); hydroxypropyl cellulose SL (HPC-SL); hydroxypropyl cellulose L (HPC-L); hydroxyethyl cellulose; a polyvinyl caprolactam-polyvinyl acetate-polyethylene glycol graft copolymer (PCL-PVAc-PEG, e.g., Soluplus®)); a polyoxylglyceride (e.g., a caprylocaproyl polyoxylglyceride, a lauroyl polyoxylglyceride (e.g., Gelucire 44/14), linoleoyl polyoxylglyceride, oleoyl polyoxylglyceride, and stearoyl polyoxylglyceride); an ethyl cellulose; a D-alpha-tocopheryl polyethylene glycol 1000 succinate; a cellulose acetate phthalate, a carboxymethylethyl cellulose and the like; a cyclodextrin (e.g., alpha-cyclodextrin, beta-cyclodextrin, gamma-cyclodextrin, and the like); a substituted cyclodextrin (e.g., a hydroxyalkyl ether cyclodextrin (e.g., hydroxypropyl-β-cyclodextrin having a degree of substitution of about 0.4-1.5 hydroxypropyl groups per anhydroglucose unit (see Handbook at 314-315), a sulfoalkyl ether cyclodextrin or a pharmaceutically acceptable salt thereof, such as, for example, a sulfobutyl ether β-cyclodextrin (viz., SBE-β-CD) or a pharmaceutically acceptable salt thereof having a degree of substitution of about 6 to 7, e.g., SBE(6-7)β-CD (see Mosher; see also Handbook at 714-717) or a substituted β-cyclodextrin, such as sugammadex (i.e., 6-per-deoxy-6-per-(2-carboxyethyl)thio-γ-cyclodextrin or a pharmaceutically acceptable salt thereof, see, e.g., Zhang and Coello); a gelatin; a hypromellose phthalate; a sugar; a polyhydric alcohol and the like; a water soluble sugar excipient (preferably having low hygroscopicity, which include, but are not limited to mannitol, lactose, fructose, sorbitol and the like); a polyethylene oxide; a polyoxyethylene derivative; a polyvinyl alcohol; a propylene glycol derivative and the like; an organic amine such as an alkyl amine (primary, secondary, and tertiary); an aromatic amine; an alicyclic amine; a cyclic amine; an aralkyl amine; a hydroxylamine or its derivatives; hydrazine or its derivatives; guanidine or its derivatives; or any other excipient at any aspect of present application. A thorough discussion of pharmaceutically acceptable excipients is presented in Remington's, the Handbook, Sarode, and EFSA Panel.

In one aspect, the solid dispersion comprising pitolisant hydrochloride and one or more pharmaceutically acceptable excipients has an amount of pitolisant hydrochloride that ranges from about 1% w/w to about 99% w/w of the solid dispersion, including all values in between, including, for example, 5% w/w, 10% w/w, 15% w/w, 20% w/w, 25% w/w, 30% w/w, 35% w/w, 40% w/w, 45% w/w, 50% w/w, 55% w/w, 60% w/w, 65% w/w, 70% w/w, 75% w/w, 80% w/w, 85% w/w, 90% w/w, and 95% w/w.

The use of mixtures of more than one of the pharmaceutical excipients to provide a desired release profile or for the enhancement of stability is within the scope of this invention. Also, all viscosity grades, molecular weights, commercially available products, their copolymers, and mixtures are all within the scope of this invention without limitation. Solid dispersions of the present application also include the solid dispersions obtained by combining pitolisant hydrochloride salt with a suitable non-polymeric excipient by employing techniques known in the art or procedures described or exemplified in any aspect of the instant invention.

Another embodiment relates to a process for preparing a solid dispersion comprising pitolisant hydrochloride and one or more pharmaceutically acceptable excipients, which comprises:

a. providing pitolisant first salt;
b. treating pitolisant first salt with base to obtain pitolisant free base;
c. treating pitolisant free base with hydrochloric acid to obtain pitolisant hydrochloride solution;
d. adding one or more pharmaceutically acceptable excipients;
e. optionally stirring the reaction mass;
f. removing the solvent from the reaction mass; and
g. isolating solid dispersion of pitolisant hydrochloride; wherein the reaction is carried out without isolation of pitolisant hydrochloride salt.

In one aspect of the process for preparing the solid dispersion disclosed herein, the first salt of pitolisant is an acid formed by reacting pitolisant with acid which is capable to form salt with pitolisant and it is selected from but not limited to hydrobromic acid, hydroiodic acid, oxalic acid, fumaric acid, maleic acid, succinic acid, acetic acid, adipic acid, ascorbic acid, aspartic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutamic acid, glutaric acid, glycerophosphoric acid, glycolic acid, hippuric acid, isobutyric acid, lactic acid, lactobionic acid, lauric acid, maleic acid, malic acid, malonic acid, mandelic acid, naphthalene-1,5-disulfonic acid, naphthalene-2-sulfonic acid, nicotinic acid, nitric acid, oleic acid, oxalic acid, palmitic acid, pamoic acid, pyroglutamic acid, salicylic acid, sebacic acid, stearic acid, succinic acid, tartaric acid, thiocyanic acid, undecylenic acid, aminocaproic acid, caprilic acid, alpha lipoic acid, R-lipoic acid, myristic acid, myristoleic acid, palmitoleic acid, elaidic acid, linoleic acid, linolenic acid, linolelaidic acid, and arachidonic acid. In one aspect, the first salt of pitolisant is an acid formed by reacting pitolisant oxalic acid and/or fumaric acid.

One will appreciate that the amount of acid used to form the first salt of pitolisant may depend on the acid equivalents available from the acid. For instance, acetic acid has one acid equivalent, oxalic acid has two acid equivalents, and citric acid has three acid equivalents. Accordingly, the mole-amount of acid, relative to the mole-amount of pitolisant, may range from about 0.3 equivalents to about 1.5 equivalents, and all values in between, including, for example about 0.4 equivalents, about 0.5 equivalents, about 0.6 equivalents, about 0.7 equivalents, about 0.8 equivalents, about 0.9 equivalents, about 1.0 equivalents, about 1.1 equivalents, about 1.2 equivalents, about 1.3 equivalents, and about 1.4 equivalents.

In another aspect of the process for preparing the solid dispersion disclosed herein, the hydrochloric acid used in the reaction is hydrochloric acid (HCl) gas or it is dissolved in water or solvent which is selected from methanolic HCl, isopropanolic HCl, ethylacetate HCl, and the like.

In another aspect of the process for preparing the solid dispersion disclosed herein, the base used in step b) is an inorganic base and/or an organic base selected from sodium hydroxide, potassium hydroxide, lithium hydroxide, sodium carbonate, potassium carbonate, lithium carbonate, sodium bicarbonate, potassium bicarbonate, lithium bicarbonate, trimethylamine, diisopropylamine, and a combination thereof.

In another aspect of the process for preparing the solid dispersion disclosed herein, said process comprises removing solvent from the reaction mass which is carried out by evaporation (e.g., distillation under ambient pressure or reduced pressure) or spray drying.

Another aspect of the present disclosure relates to a process for preparing a solid dispersion comprising pitolisant hydrochloride and one or more pharmaceutically acceptable excipients, said process comprising:
a) providing solution of pitolisant hydrochloride salt in a suitable solvent;
b) adding one or more pharmaceutically acceptable excipients;
c) removing the solvent; and
d) isolating an amorphous solid dispersion of pitolisant hydrochloride In another embodiment, pitolisant hydrochloride salt may be combined with one or more pharmaceutically acceptable excipients, at room temperature or under heating or mechanical stress to obtain molten mixture of components.

In one aspect, the molten mixture may be optionally cooled to obtain solid dispersion of pitolisant hydrochloride salt with one or more pharmaceutically acceptable excipients. In one aspect, pitolisant hydrochloride may be combined with one or more pharmaceutically acceptable excipients in suitable equipment such as hot melt extruder, twin screw extruder or the like.

In another aspect, pitolisant hydrochloride salt may be combined with one or more pharmaceutically acceptable excipients in presence of a suitable solvent selected from the list of solvents, including, a protic solvent, an aprotic solvent, a polar aprotic solvent, and a combination thereof. Selected solvents include, but are not limited to N,N-dimethylformamide, N,N-dimethylacetamide, dimethyl-sulfoxide, 1-methyl-2-pyrrolidone, 1-methyl-2-piperidone, 1,3-dimethyl-2-imidazolidinone, acetonitrile, acetone, dichloromethane, ethyl acetate, tetrahydrofuran, acetone, methanol, ethanol, isopropanol, water, and a combination thereof.

In another aspect, one or more pharmaceutically acceptable excipients of this aspect may be selected from pharmaceutically acceptable excipients disclosed herein.

In other aspects, combining pitolisant hydrochloride salt may be carried out by dissolving pitolisant hydrochloride salt and one or more pharmaceutically acceptable excipients simultaneously or separately in same or different solvents.

In another aspect, a solution of pitolisant hydrochloride salt and the one or more pharmaceutical acceptable excipients may be prepared at any suitable temperature, at about 0° C. to the reflux temperature of the solvent used. Stirring and heating may be used to reduce the time required for the dissolution process.

In another aspect, a solution of pitolisant hydrochloride salt and the excipient may be filtered to make it clear and free of unwanted particles. In embodiments, the obtained solution may be optionally treated with an adsorbent material, such as carbon and/or hydrose, to remove coloured components, etc., before filtration.

In another aspect, the solid dispersion comprising pitolisant hydrochloride and one or more pharmaceutically acceptable excipients may be prepared without isolating pitolisant hydrochloride salt from the reaction mass and the one or more pharmaceutically acceptable excipients was added to the solution of pitolisant hydrochloride which is obtained directly from the reaction mass followed by removal of solvent from the reaction mass.

In another aspect, the solvent from the solution of pitolisant hydrochloride salt and the one or more pharmaceutically acceptable excipients may be removed as per the methods described herein.

In another aspect, the solid dispersion comprising pitolisant hydrochloride and one or more pharmaceutically acceptable excipients may be isolated as per the methods described herein.

In yet another aspect, the solid dispersion disclosed herein exhibits physicochemical stability under thermal, humid and stress conditions. In this regard, the solid dispersion comprising pitolisant hydrochloride exhibits a degree of amorphicity that ranges from about 80% to about 100% and all values in between, including about 85%, about 90%, about 95%, about 98%.

In certain aspects, the solid dispersion may comprise a pitolisant hydrochloride hydrate as disclosed herein, for example, pitolisant hydrochloride sesquihydrate, wherein the solid dispersion has no pitolisant hydrochloride monohydrate and no crystalline pitolisant hydrochloride monohydrate. In another aspect, the solid dispersion may comprise a pitolisant hydrochloride hydrate as disclosed herein, for example, pitolisant hydrochloride dihydrate, wherein the solid dispersion has no pitolisant hydrochloride having a water content of 2.7 to 6.5%

In certain aspects, the solid dispersion may comprise an amorphous form of pitolisant hydrochloride exhibiting a degree of amorphicity of about 100%, where the solid dispersion does not comprise any crystalline pitolisant hydrochloride.

In one aspect, the amorphous form of pitolisant hydrochloride may be prepared by evaporating a solvent comprising the pitolisant hydrochloride and the one or more pharmaceutically acceptable excipients by freeze drying, distillation, and spray drying.

In yet another aspect, the amorphous form of pitolisant may be prepared by combining a solid-state form of pitolisant hydrochloride and one or more pharmaceutically acceptable exhibits by milling, e.g., by ball milling.

In another aspect, the amorphous form of pitolisant hydrochloride may be prepared by a process that does not include isolating solid pitolisant hydrochloride and the solution obtained from the reaction medium is directly spray dried or freeze dried.

In another aspect of the present disclosure, the amorphous solid dispersion comprises pitolisant hydrochloride and beta-cyclodextrin present in the ratio from about 1:0.5 to 1:10 (viz., a pitolisant hydrochloride amount of about 9% to about 66% by weight of the solid dispersion). In yet another aspect, the amorphous solid dispersion comprises pitolisant hydrochloride and beta-cyclodextrin in the ratio of about 1:1 to 1:5. In a further aspect, the amorphous solid dispersion comprises pitolisant hydrochloride and beta-cyclodextrin in the ratio of about 1:1 to 1:3.

In another aspect, the amorphous solid dispersion comprises pitolisant hydrochloride and povidone in the ratio from about 1:0.1 to 1:5. In yet another aspect, the amorphous solid dispersion comprises pitolisant hydrochloride and povidone in the ratio of about 1:0.2 to 1:1. In a further aspect, the amorphous solid dispersion comprises pitolisant hydrochloride and povidone in the ratio of about 1:0.3.

In another aspect, the amorphous solid dispersion comprises pitolisant hydrochloride and copovidone in the ratio from 1:0.5 to 1:10. In yet another aspect, the amorphous solid dispersion comprises pitolisant hydrochloride and povidone in the ratio of about 1:1 to 1:5. In a further aspect, the amorphous solid dispersion comprises pitolisant hydrochloride and povidone in the ratio of about 1:2 to 1:3.

Another aspect relates to pitolisant hydrochloride sesquihydrate and beta-cyclodextrin solid dispersion is characterised by PXRD peaks at 5.3, 7.3, 10.0, and 11.8±0.2° two-theta. In another aspect of the present disclosure relates to pitolisant hydrochloride sesquihydrate and beta-cyclodextrin solid dispersion is characterised by PXRD additional peaks at 10.7 and 17.3±0.2° two-theta (2θ). The following table identifies PXRD characteristic peaks of a solid dispersion comprising pitolisant hydrochloride sesquihydrate and beta-cyclodextrin solid dispersion.

| Pos. [°2θ] | Height [cts] | d-spacing [Å] | Rel. Int. % |
|---|---|---|---|
| 2.5927 | 5365.03 | 34.07666 | 41.85 |
| 5.3278 | 1736.86 | 16.58758 | 13.55 |
| 7.3655 | 1552.72 | 12.00237 | 12.11 |
| 8.8318 | 977.45 | 10.01277 | 7.62 |
| 10.0824 | 2008.11 | 8.77345 | 15.66 |
| 10.7396 | 3448.85 | 8.23795 | 26.9 |
| 11.8583 | 2801.55 | 7.46321 | 21.85 |
| 13.9931 | 1860.99 | 6.32905 | 14.52 |
| 14.8457 | 3131.98 | 5.96742 | 24.43 |
| 17.3201 | 12820.42 | 5.12007 | 100 |
| 18.2166 | 11877.29 | 4.87006 | 92.64 |
| 18.8275 | 9856.15 | 4.7134 | 76.88 |
| 19.4633 | 7823.79 | 4.56084 | 61.03 |
| 21.8923 | 4410.67 | 4.06 | 34.4 |
| 23.2112 | 3279.61 | 3.83219 | 25.58 |
| 23.9621 | 3274.47 | 3.71377 | 25.54 |
| 24.8843 | 2122.66 | 3.5782 | 16.56 |
| 38.354 | 1202.75 | 2.34693 | 9.38 |

Another aspect relates to a solid dispersion comprising pitolisant hydrochloride sesquihydrate and a β-cyclodextrin having a PXRD pattern substantially as shown in FIG. 4.

Another aspect disclosed herein relates to a co-crystal form of pitolisant hydrochloride comprising pitolisant hydrochloride and pharmaceutically acceptable co-former.

In one aspect, the co-former is a "pharmaceutically acceptable co-former". The term "pharmaceutically acceptable co-former" refers to a co-former suitable for use as a pharmaceutical agent in the preparation of compositions with medical use. It must also be suitable for use in contact with the tissue or organ of humans and animals without excessive toxicity, irritation, allergic response, immunogenicity or other problems or complications commensurate with a reasonable benefit/risk ratio.

In another aspect, co-former is selected from succinic acid, benzoic acid, ketoglutaric acid, maleic acid, malonic acid, adipic acid, oxalic acid, piperazine, succinimide, benzenesulfonamide, proline, L-proline, D-proline, (+) camphoric acid, L-pyroglutamic acid, L-aspartic acid, L-carnitine, citric acid, 4-hydroxybenzoic acid, L-glutamic acid, nicotinamide, nicotinic acid, orotic acid monohydrate, urea, tetraethylpyrazine, tetraethylpyrazine, acetyl salicylic acid, 4-aminobenzoic acid, cinnamic acid, salicylic acid, ferulic acid, methylgallate, thiourea, saccharin, methylparaben, propyl gallate, vanillin, or a combination thereof.

In one aspect, the co-crystal form may be prepared from a pitolisant hydrochloride solid-state form by, e.g., mixing or grinding the pitolisant hydrochloride solid state form with a pharmaceutically acceptable co-former. Alternatively, the co-crystal form may be prepared by contacting the pitolisant hydrochloride solid-state form and the pharmaceutically acceptable co-former in the presence of a suitable solvent (with or without a suitable anti-solvent).

Another embodiment relates to a pitolisant oxalate having characteristic PXRD peaks at 7.4, 14.8, 21.8, 22.3, and 29.8±0.2° 2θ. The following table identifies PXRD characteristic peaks of pitolisant oxalate.

| Pos. [°2θ] | Height [cts] | d-spacing [Å] | Rel. Int. [%] |
|---|---|---|---|
| 7.4291 | 463033.90 | 11.89973 | 100.00 |
| 12.3183 | 9292.82 | 7.18553 | 2.01 |
| 14.8465 | 386446.80 | 5.96711 | 83.46 |
| 15.8472 | 13720.65 | 5.59246 | 2.96 |
| 16.9819 | 14230.37 | 5.22127 | 3.07 |
| 17.8909 | 21080.13 | 4.95798 | 4.55 |
| 18.7984 | 35910.07 | 4.72063 | 7.76 |
| 20.0640 | 15832.79 | 4.42564 | 3.42 |
| 20.4440 | 24899.65 | 4.34423 | 5.38 |
| 21.0431 | 11937.36 | 4.22188 | 2.58 |
| 21.8673 | 143549.70 | 4.06457 | 31.00 |
| 22.3148 | 457750.90 | 3.98408 | 98.86 |
| 23.4047 | 31338.30 | 3.80095 | 6.77 |
| 23.9117 | 11474.29 | 3.72150 | 2.48 |
| 24.2867 | 11744.37 | 3.66487 | 2.54 |
| 24.7483 | 17105.59 | 3.59756 | 3.69 |
| 25.1743 | 16448.12 | 3.53763 | 3.55 |
| 29.8686 | 97167.32 | 2.99147 | 20.98 |
| 35.6951 | 14104.91 | 2.51541 | 3.05 |

Another aspect relates to a pitolisant oxalate having a PXRD pattern substantially as shown in FIG. 6.

Another embodiment relates to a pitolisant hydrochloride hydrate of Formula-(II)

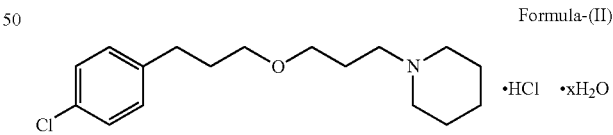

Formula-(II)

wherein x is 1.5, 2, 2.5, 3, or 5.

One aspect relates to pitolisant hydrochloride of Formula-(II), where x is 1.5. For this aspect, the pitolisant hydrochloride of Formula-(II) (viz., pitolisant hydrochloride sesquihydrate) has a water content of about 7.7% w/w.

Another aspect relates to pitolisant hydrochloride of Formula-(II), where x is 2. For this aspect, the pitolisant hydrochloride of Formula-(II) (viz., pitolisant hydrochloride dihydrate) has a water content of about 9.8% w/w.

Yet another aspect relates to pitolisant hydrochloride of Formula-(II), where x is 2.5. For this aspect, the pitolisant hydrochloride of Formula-(II) (viz., pitolisant hydrochloride hemipentahydrate) has a water content of about 12.3% w/w.

Another aspect relates to pitolisant hydrochloride of Formula-(II), where x is 3. For this aspect, the pitolisant hydrochloride of Formula-(II) (viz., pitolisant hydrochloride hemipentahydrate) has a water content of about 14.4% w/w.

Another aspect relates to pitolisant hydrochloride of Formula-(II), where x is 5. For this aspect, the pitolisant hydrochloride of Formula-(II) (viz., pitolisant hydrochloride pentahydrate) has a water content of about 21.2% w/w.

One embodiment relates to crystalline pitolisant hydrochloride sesquihydrate. The pitolisant hydrochloride sesquihydrate has PXRD peaks at 5.3, 7.3, 10.0, 11.8, and 26.1±0.2° two-theta. The following table identifies PXRD characteristic peaks of pitolisant hydrochloride sesquihydrate.

| Pos. [°2θ] | Height [cts] | d-spacing [Å] | Rel. Int. [%] |
|---|---|---|---|
| 2.5927 | 18403.52 | 34.07666 | 73.65 |
| 3.5717 | 7677.55 | 24.73828 | 30.72 |
| 5.3288 | 14096.36 | 16.58421 | 56.41 |
| 7.3504 | 10951.39 | 12.02702 | 43.83 |
| 8.8165 | 9327.8 | 10.03012 | 37.33 |
| 10.0682 | 10286.64 | 8.78573 | 41.16 |
| 10.7554 | 14475.28 | 8.22588 | 57.93 |
| 11.122 | 10077.4 | 7.95559 | 40.33 |
| 11.4731 | 4465.08 | 7.71287 | 17.87 |
| 11.8611 | 7119.93 | 7.46145 | 28.49 |
| 13.5558 | 4984.79 | 6.53219 | 19.95 |
| 13.9512 | 5083.19 | 6.34793 | 20.34 |
| 14.3887 | 4450.58 | 6.15592 | 17.81 |
| 14.8492 | 7864.84 | 5.96604 | 31.47 |
| 15.2756 | 8072.94 | 5.80042 | 32.31 |
| 16.1671 | 10343.51 | 5.48254 | 41.39 |
| 16.6405 | 8990.31 | 5.32762 | 35.98 |
| 17.3118 | 24988.85 | 5.1225 | 100 |
| 17.6405 | 19917.73 | 5.0278 | 79.71 |
| 18.2575 | 13662.01 | 4.85925 | 54.67 |
| 18.9197 | 12081.32 | 4.69063 | 48.35 |
| 19.545 | 11561.28 | 4.54197 | 46.27 |
| 19.7524 | 10840.44 | 4.49474 | 43.38 |
| 20.6094 | 19244.05 | 4.30972 | 77.01 |
| 21.6246 | 9720.31 | 4.10964 | 38.9 |
| 21.9331 | 9190.48 | 4.05254 | 36.78 |
| 23.9792 | 6927.88 | 3.71118 | 27.72 |
| 24.9208 | 10513.97 | 3.57304 | 42.07 |
| 25.3733 | 11578.26 | 3.51034 | 46.33 |
| 26.1062 | 6663.5 | 3.41343 | 26.67 |
| 27.1049 | 4072.53 | 3.28989 | 16.3 |
| 28.7549 | 4600.36 | 3.10475 | 18.41 |
| 29.1258 | 3122.82 | 3.06605 | 12.5 |
| 30.1217 | 2517.8 | 2.96691 | 10.08 |
| 30.6702 | 3190.6 | 2.9151 | 12.77 |
| 33.8038 | 2853.36 | 2.6495 | 11.42 |
| 33.9292 | 2810.7 | 2.64218 | 11.25 |
| 34.8873 | 3285.97 | 2.57178 | 13.15 |
| 35.5094 | 4266.61 | 2.52814 | 17.07 |

Another aspect relates to a pitolisant hydrochloride sesquihydrate having a PXRD pattern substantially as shown in FIG. 5.

In another aspect of the present disclosure provides a process for preparing pitolisant hydrochloride sesquihydrate comprising:
a. providing pitolisant first salt;
b. neutralising pitolisant first salt to obtain pitolisant free base;
c. treating pitolisant free base with hydrochloride to obtain pitolisant hydrochloride solution;
d. optionally adding water to the reaction mass;
e. removing the solvent; and
f. isolating pitolisant hydrochloride.

In one more embodiment of the present disclosure provides a method for preparing hydrate forms of pitolisant hydrochloride by dissolving pitolisant hydrochloride of Formula-(I) in water or mixture of water and organic solvent, optionally treating with carbon, filtering and precipitating the solid by adding solvent in which pitolisant hydrochloride is not soluble.

In one more embodiment of the present disclosure provides a method for preparing a pitolisant hydrochloride hydrate form comprising
a) providing a solution on pitolisant hydrochloride
b) removing solvent from the reaction mass to obtain solid wherein the removal of solvent from the reaction mass is carried out by evaporation, spray drying, air drying, freeze drying, etc.

In one more embodiment of the disclosure provides a solution of pitolisant hydrochloride is prepared by dissolving pitolisant hydrochloride in water alone or mixture of water and solvent wherein the solvent is selected from methanol, ethanol, isopropanol, butanol, dichloromethane, dimethylformamide, and dimethylsulfoxide.

The starting material particularly 3-(4-chlorophenyl)-propanol of Formula-(V) for the preparation of pitolisant hydrochloride of Formula-(I) in the present disclosure is prepared by conventional methods or methods as disclosed herein.

One embodiment relates to the preparation of 3-(4-chlorophenyl)-propanol of Formula-(V), as depicted in Scheme-4.

Scheme-4

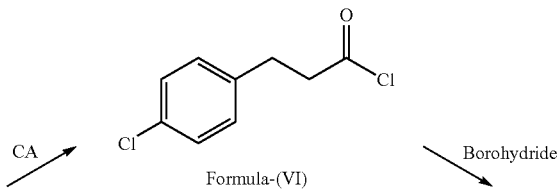

Formula-(VI)

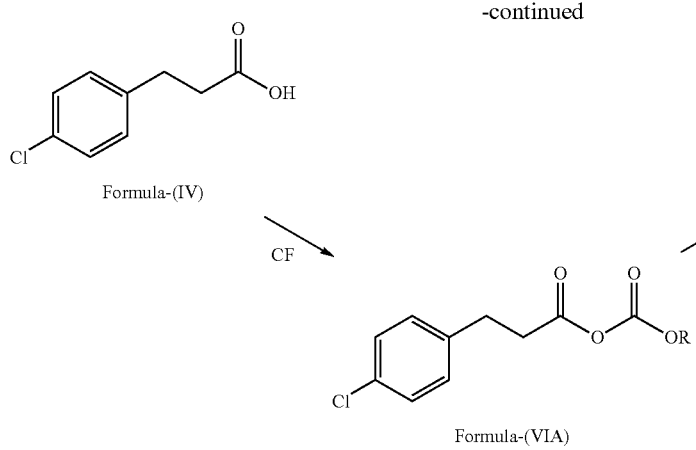

Formula-(IV)    CF    Formula-(VIA)    Borohydride    Formula-(V)

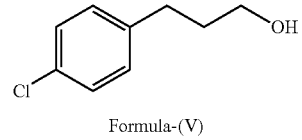

In Scheme-4, the chlorinating agent (CA) may be any suitable agent that converts the carboxylic acid moiety of Formula-(IV) to a carboxylic acid chloride of Formula-(VI). Examples of chlorinating agents include, but are not limited to, phosgene ($C(O)Cl_2$), diphosgene ($Cl_3COC(O)Cl$), triphosgene ($Cl_3COC(O)OCCl_3$), thionyl chloride ($S(O)Cl_2$), oxalyl chloride ($ClC(O)$—$C(O)Cl$), phosphorus oxychloride ($P(O)Cl_3$), etc.

Also, in Scheme-4, the chloroformate (CF or $ClC(O)OR$) may be any suitable agent that converts the carboxylic acid moiety of Formula-(IV) to the carboxylic acid anhydride of Formula-(VIA), where the R-group for Formula-(VIA) may be any suitable radical (e.g., alkyl group or phenyl), including, for example a linear or branched alkyl having 1 to 12 carbon atoms, including for example, methyl, ethyl, propyl, isopropyl, isobutyl and the like (e.g., a Ci-6 alkyl); or in the instance of a phenyl, R may be a unsubstituted phenyl or a substituted phenyl (e.g., o-tolyl, xylyl, etc.).

In the view of the foregoing, an embodiment relates to the preparation of 3-(4-chlorophenyl)-propanol of Formula-(V), comprising a) providing 3-(4-chlorophenyl)-propionic acid of Formula-(IV) in a solvent;

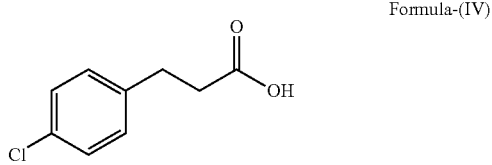 [SMILES: O=C(O)CCc1ccc(Cl)cc1]

Formula-(IV)

b) converting 3-(4-chlorophenyl)-propionic acid of Formula-(IV) to its acid chloride of Formula-(VI) or acid anhydride Formula-(VIA); and

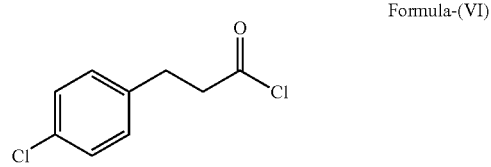

Formula-(VI)

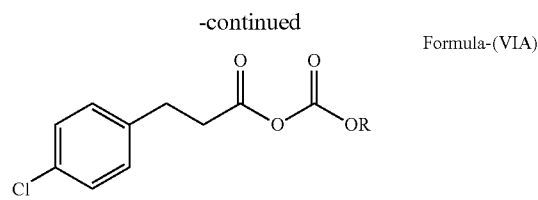

Formula-(VIA)

c) reducing acid chloride of Formula-(VI) or acid anhydride Formula-(VIA) to obtain 3-(4-chlorophenyl)-propanol of Formula-(V)

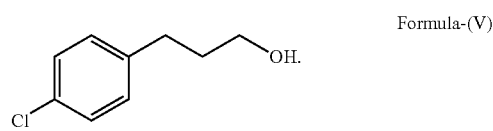 [SMILES: OCCCc1ccc(Cl)cc1]

Formula-(V)

In one aspect, the 3-(4-chlorophenyl)-propionic acid of step a) is dissolved in solvent selected from dichloromethane, dichloroethane, tetrahydrofuran, toluene, dioxane, N,N-dimethylformamide, N,N-dimethylacetamide, dimethylsulfoxide, 1-methyl-2-pyrrolidone, 1-methyl-2-piperidone, 1,3-dimethyl-2-imidazolidinone, acetonitrile, acetone, ethyl acetate, methanol, ethanol, isopropanol, n-butanol, and combination thereof.

In another aspect, the conversion of 3-(4-chlorophenyl)-propionic acid of Formula-(IV) to its acid chloride of Formula-(VI) is carried out in presence of a chlorinating agent, including, for example, phosgene ($C(O)Cl_2$), diphosgene ($Cl_3COC(O)Cl$), triphosgene ($Cl_3COC(O)OCCl_3$), thionyl chloride ($S(O)Cl_2$), oxalyl chloride ($ClC(O)$—$C(O)Cl$), phosphorus oxychloride ($P(O)Cl_3$), etc.

In yet another aspect, the conversion of 3-(4-chlorophenyl)-propionic acid of Formula-(IV) to its acid anhydride of Formula-(VIA) is carried out in presence of a haloformate selected from methylchloroformate, ethylchloroformate, isopropyl chloroformate, isobutyl chloroformate, phenyl chloroformate, etc.

In another aspect, the reaction of step b) is carried out in presence of solvent selected from dichloromethane, dichloroethane, tetrahydrofuran, toluene, dioxane, N,N-dimethylformamide, N,N-dimethylacetamide, dimethylsulfoxide, 1-methyl-2-pyrrolidone, 1-methyl-2-piperidone, 1,3-dimethyl-2-imidazolidinone, acetonitrile, acetone, ethyl acetate, methanol, ethanol isopropanol, n-butanol, and a combination thereof.

In yet another aspect, the reduction reaction of step c) is carried out in presence of a borohydride selected from lithium borohydride, sodium borohydride, potassium borohydride, sodium cyanoborohydride, lithium triethyl borohydride, and a combination thereof. In one aspect, the reduction reaction of step c) is carried out in the presence of sodium borohydride.

One will appreciate that the reagents may be used in an amount corresponding to a about 1-mole equivalent based on the reactant. For instance, in the conversion of 3-(4-chlorophenyl)-propionic acid of Formula-(IV) to its acid chloride of Formula-(VI) or acid anhydride Formula-(VIA), one will appreciate that the amount of chlorinating agent or chloroformate will be based on the amount of 3-(4-chlorophenyl)-propionic acid. Accordingly, reaction of about 1 mol of 3-(4-chlorophenyl)-propionic acid may require about 1 mol of chlorinating agent or about 1 mol of chloroformate. In certain instances, it may be desirable to use an excess of chlorinating agent or chloroformate, e.g., 1.05-mol excess, 1.1-mol excess, and the like. The same reasoning may be applicable with respect to a borohydride used in step c).

In another aspect, the reduction reaction of step c) is carried out in same solvent as used in step b) and in optionally presence of water.

In another aspect, the reduction reaction of step c) is carried out at a temperature in the range of 0° C. to 25° C.

In another aspect, the acid chloride or anhydride formation and reduction reaction of steps b) and reduction step c) are carried out with or without isolating acid chloride or anhydride.

In another embodiment of the present disclosure, the pitolisant hydrochloride obtained from processes disclosed herein is substantially pure and has a chemical purity ≥98%, ≥98.5%, ≥99%, ≥99.5%, ≥99.6%, ≥99.7%, ≥99.8%, ≥99.9%, or ≥99.98% as determined by HPLC. In another aspect of the present invention, pitolisant hydrochloride obtained from present disclosure is essentially free of deschloro impurities selected from compounds of Formula-(VA), deschloro mesyl compound of Formula-(IIIA) and deschloro pitolisant of Formula-(IA)

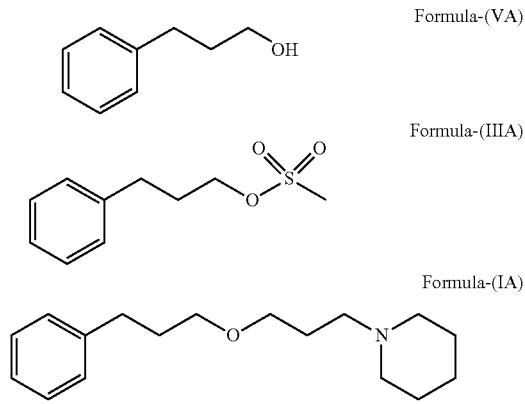

Formula-(VA)

Formula-(IIIA)

Formula-(IA)

In another embodiment of the present disclosure, the composition comprising pitolisant hydrochloride obtained from processes described herein has total impurities less than 1.0% less than 0.5%, or less than 0.2%, based on the total weight of the composition.

Still another embodiment of the present disclosure, the composition comprising pitolisant hydrochloride obtained from processes described herein has less than 1.0% of deschloro impurities selected from compounds of Formula-(VA), deschloro mesyl compound of Formula-(IIIA), and deschloro pitolisant of Formula-(IA).

HPLC purity of pitolisant hydrochloride obtained by processes disclosed herein may be greater than or equal to 98% by weight of the composition, as evidenced by the following results of a representative sample.

| | |
|---|---|
| Assay by HPLC (% w/w) | 99.6% |
| Related Substances by HPLC (% w/w): | |
| Benzyl amino alcohol[a] | Not detected |
| Benzyl piperazine[b] | Not detected |
| N-oxide[c] | Not detected |
| Des impurity[d] | Not detected |
| Highest unspecified impurity | 0.03% w/w |
| Total impurities | 0.05% w/w |

Notes:
[a]Benzyl amino alcohol (1-[3-(4-Chloro-benzyloxy)-propyl]-piperidine)
[b]Benzyl piperazine (1-(4-Chloro-benzyl)-piperidine)
[c]N-oxide (1-{3-[3-(4-Chloro-phenyl)-propoxy]-propyl}-piperidine 1-oxide)
[d]Des impurity (Deschloro pitolisant)

Disclosed herein is a pharmaceutical composition (e.g., tablet, capsule, or suspension) for administration of a therapeutically effective amount of pitolisant to a patient in need thereof for the treatment of excessive daytime sleepiness (EDS) or cataplexy in adult patients with narcolepsy. In one aspect, the pharmaceutical compositions may include one or more of an excipient selected from a carrier, a filler, a diluent, a suspending agent, a lubricant, a glidant, a sweetener, a stabilizing agent, a solubilizing agent, an antioxidant, a preservative, a flavoring agent, a binder, a colorant, an osmotic agent, a buffer, a surfactant, a disintegrant, a granulating agent, and a coating material. For instance, the pharmaceutical composition (e.g., tablet) may comprise a therapeutically effective amount of pitolisant (e.g., about 4.45 mg or about 17.8 mg), an excipient, and a coating layer.

In one aspect, the pharmaceutical composition disclosed herein comprises any one of the solid-state forms of pitolisant hydrochloride disclosed herein, such as, for example, pitolisant hydrochloride dihydrate, pitolisant hydrochloride sesquihydrate (including crystalline pitolisant hydrochloride sesquihydrate), pitolisant hydrochloride hemipentahydrate, pitolisant hydrochloride trihydrate, pitolisant hydrochloride pentahydrate, or a combination thereof and an excipient.

In another aspect, the pharmaceutical composition disclosed herein comprises any one of the solid dispersions disclosed herein, such as, for example, a solid dispersion comprising pitolisant hydrochloride and one or more pharmaceutically acceptable excipients (e.g., beta-cyclodextrin, povidone, copovidone, HMPC, HMPC-AS, PEG 4000, PEG-6000, PVP, CSD, and the like) and an excipient.

One embodiment relates to a method of treating EDS or cataplexy in a narcoleptic adult, which comprises administering a therapeutically effective amount of pitolisant to an adult in need thereof, as disclosed in the WAKIX® Label.

One aspect relates to a method of treating EDS or cataplexy in a narcoleptic adult, which comprises administering a pharmaceutical composition disclosed herein comprising about 4.45 mg pitolisant and an excipient.

Yet another aspect relates to a method of treating EDS or cataplexy in a narcoleptic adult, which comprises administering a pharmaceutical composition disclosed herein comprising about 17.8 mg pitolisant and an excipient.

EXAMPLES

The present disclosure is provided by the examples below, which are provided by way of illustration only and should not be considered to limit the scope of this invention.

Powder X-Ray Diffraction

Powder X-ray diffraction was carried out on a PANalytical diffractometer, scanning the samples between 2.51 and 49.9° 2-theta. About 500-600 mg of material was gently compressed onto a glass disc inserted into a PXRD sample holder. The sample was then loaded into the diffractometer running in reflection mode and analyzed using the following experimental conditions.

| Raw Data Origin | XRD measurement (*.XRDML) |
|---|---|
| Scan Axis | Gonio |
| Start Position [°2θ] | 2.5147 |
| End Position [°2θ] | 49.9777 |
| Step Size [°2θ] | 0.0390 |
| Scan Step Time [s] | 164.9850 |
| Scan Type | Continuous |
| PSD Mode | Scanning |
| PSD Length [°2θ] | 3.35 |
| Offset [°2θ] | 0.0000 |
| Divergence Slit Type | Fixed |
| Divergence Slit Size [°] | 0.3599 |
| Specimen Length [mm] | 10.00 |
| Measurement Temperature [° C.] | 25.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 30 mA, 45 kV |
| Diffractometer Type | 0000000011222148 |
| Diffractometer Number | 0 |
| Goniometer Radius [mm] | 240.00 |
| Dist. Focus-Diverg. Slit [mm] | 60.50 |
| Incident Beam Monochromator | No |
| Spinning | No |

Chromatographic Conditions

A high-performance liquid chromatography equipped with ultraviolet spectrometer as a detector and an auto sampler.

| Column details | Water's symmetry C18 (250 mm × 4.6 mm, ID 5 µm) |
|---|---|
| Flow rate | 1.0 mL/min (Gradient) |
| Wavelength | UV at 220 nm |
| Column temperature | 45° C. |
| Injection volume | 20 µL |
| Diluent | Water and Methanol |
| Run time | 60 minutes |

Water Content Determination by KF (% w/w)

Transfer a sufficient quantity of methanol (approximately 30 to 40 mL), to the titration vessel, ensuring that the electrodes dipped in the methanol and neutralize with the Karl Fischer reagent to the electrometric end point to consume any moisture that may be present. Quickly add about 0.2 g sample accurately weighed, mix and again titrate with the Karl Fischer reagent to the electrometric end point. Calculate the water content in % w/w.

$$\text{Water content } (\% \ w/w) = \frac{\text{Titer volume} \times \text{water equivalence factor} \times 100}{\text{Sample taken in gram} \times 1000}$$

Example 1. Pitolisant Hydrochloride

To 100 g of N,N-dimethylacetamide, 12 g of potassium tertiary butoxide was added under stirring. To the reaction mass 3-(piperidin-1-yl)propan-1-ol was added under stirring and the reaction mass was heated to 50-60° C. and stirred for 60 minutes. The reaction mass was cooled to room temperature and stirred for 15 minutes. To the reaction mass a solution of 3-(4-chlorophenyl) propyl methanesulfonate dissolved in N,N-dimethylacetamide was added and stirred for 12-14 hours. The reaction mass was cooled to 0-5° C., sodium chloride solution was added, stirred and the reaction mass temperature was raised to room temperature. To the reaction mass toluene was added and layer was separated. To the aqueous layer toluene was added, stirred and layers were separated. To the combined organic layer dilute hydrochloride was added, stirred and layers were separated. The aqueous layer was extracted with dichloromethane, layers were separated, and the organic layer was treated with carbon, stirred filtered and bed was washed with methylene dichloride. To the filtrate sodium sulphate was added, stirred, filtered and the filtrate was distilled under vacuum. To the residue, isopropanolic hydrochloride, followed by ethyl acetate was added and solvent was distilled. To the residue, ethyl acetate was added, heated to 50-70° C. the reaction mass to get clear solution. The reaction mass was cooled to 10-25° C., stirred and filtered. The wet cake was suck dried and dried under vacuum. The obtained solid 1-{3-[3-(4-chlorophenyl)propoxy]propyl}piperidine hydrochloride was recrystallized from ethyl acetate, filtered and dried.

Example 2. Pitolisant Hydrochloride

To a mixture of methanol and sodium hydroxide solution 3-(piperidin-1-yl)propan-1-ol was added under stirring, the reaction mass was heated to 50-60° C. and stirred for 60 minutes. The reaction mass was distilled under vacuum to the residue a solution of 3-(4-chlorophenyl) propyl methanesulfonate dissolved in tetrahydrofuran was added and stirred for 12-14 hours. The reaction mass was cooled to 0-5° C., sodium chloride solution was added, stirred and the reaction mass temperature was raised to room temperature. To the reaction mass toluene was added and layer was separated. To the aqueous layer toluene was added, stirred and layers were separated. To the combined organic layer dilute hydrochloride was added, stirred and layers were separated. The aqueous layer was extracted with dichloromethane, layers were separated, and the organic layer was treated with carbon, stirred filtered and the bed was washed with methylene dichloride. To the filtrate sodium sulphate was added, stirred, filtered and the filtrate was distilled under vacuum. To the residue, isopropanolic hydrochloride, followed by ethyl acetate was added and solvent was distilled. To the residue, ethyl acetate was added, heated to 50-70° C. the reaction mass to get clear solution. The reaction mass was cooled to 10-25° C., stirred and filtered. The wet cake was suck dried and dried under vacuum. The obtained solid 1-{3-[3-(4-chlorophenyl)propoxy]propyl}piperidine hydrochloride was recrystallized from ethyl acetate, filtered and dried.

Example 3. Solid Dispersion Comprising Pitolisant Hydrochloride and Povidone 20 g of pitolisant hydrochloride was dissolved in 200 mL isopropanol, to this solution 6 g of povidone was added, stirred to get clear solution. The solution was filtered and the filtrate was spray dried to obtain amorphous solid dispersion shown in FIG. 2.

| | |
|---|---|
| Spray type: | Closed loop |
| Spray rate: | 5 mL/min |
| Chamber temperature: | 75-80° C. |

1 g of pitolisant hydrochloride was dissolved in 5 mL isopropanol, to this solution 0.3 g of povidone was added, stirred to get clear solution. The solution was distilled under vacuum at 50-60° C.

Example 4. Solid Dispersion Comprising Pitolisant Hydrochloride and Copovidone 1 g of pitolisant hydrochloride was dissolved in 50 mL isopropanol, to this solution 5 g of copovidone was added, stirred to get clear solution. The solution was filtered and the filtrate was distilled to obtain amorphous solid dispersion.

5 g of pitolisant hydrochloride was dissolved in 500 mL of isopropanol, to this solution 25 g of copovidone was added, stirred to get clear solution. The solution was spray dried to obtain amorphous solid dispersion.

Example 5. Solid Dispersion Comprising Pitolisant Hydrochloride and Beta-Cyclodextrin 75 g of beta-cyclodextrin was added to 1250 mL water and the mixture was heated to 85° C. to get clear solution, to this solution 25 g of pitolisant hydrochloride was added, stirred to get clear solution. The solution was filtered and the filtrate was spray dried to obtain amorphous solid dispersion.

| | |
|---|---|
| Spray type: | Open loop |
| Spray rate: | 5 mL/min |
| Chamber temperature: | 95-100° C. |

Example 6. Solid Dispersion Comprising Pitolisant Hydrochloride and HMPC 5 g of hydroxypropyl methylcellulose (HPMC) was dissolved in 150 mL of mixture of dichloromethane and isopropanol (3:7) by stirring to get clear solution, to this solution 1 g of pitolisant hydrochloride was added, stirred to get clear solution. The solution was distilled under vacuum at 70-80° C.

Example 7. Solid Dispersion Comprising Pitolisant Hydrochloride and HPMC-AS

Pitolisant hydrochloride (5 g) was dissolved in water (10 mL) and stirred for 30 min and added to hydroxy propyl methyl cellulose acetyl succinate (HPMC-AS) solution (5 g of HPMC-AS dissolved in 30 mL methanol). Distilled off the solvent from the mixture and then dried to provide the title composition.

Example 8. Solid Dispersion Comprising Pitolisant Hydrochloride and PEG 4000

3 g of PEG-4000 was added to 30 mL of water, heated to 80° C. to get the clear solution. To this solution 1 g of pitolisant hydrochloride was added, stirred to get clear solution. The solution was distilled under vacuum at 70-80° C.

Example 9. Solid Dispersion Comprising Pitolisant Hydrochloride and PEG 6000

3 g of PEG-6000 was dissolved in 10 mL water to get clear solution, to this solution 1 g of pitolisant hydrochloride was added, stirred to get clear solution. The solution was distilled under vacuum at 70-80° C.

3 g of PEG-6000 and 20 mL of isopropanol was heated to 50° C. to get clear solution, to this solution 1 g of pitolisant hydrochloride was added, stirred to get clear solution. The solution was distilled under vacuum at 70-80° C.

Example 10. Solid Dispersion Comprising Pitolisant Hydrochloride and PVP

Pitolisant hydrochloride (5 g) was dissolved in water (100 mL). Aqueous polyvinyl pyrrolidine (PVP) solution (5 g of PVP dissolved in 3 mL of water) was added to the above obtained solution and distilled off the solvent under reduced pressure and then dried to get the title compound.

Example 11. Solid Dispersion Comprising Pitolisant Hydrochloride and CSD

Pitolisant hydrochloride (5 g) was dissolved in water (100 ml) and stirred for 30 min. 5 g colloidal silicon dioxide (CSD (e.g., Syloid)) was added to the above solution and distilled off the solvent from the mixture and then dried to provide the title compound.

Example 12. Process for Preparing Pitolisant Hydrochloride Sesquihydrate by Spray Drying 10 g of pitolisant hydrochloride was dissolved in 100 mL water, the obtained solution was filtered and the filtrate was spray dried to obtain pitolisant hydrochloride sesquihydrate.

| | |
|---|---|
| Spray type: | Open Loop |
| Spray rate: | 5 mL/min |
| Chamber temperature: | 95-100° C. |

Example 13. Solid Dispersion Comprising Pitolisant Hydrochloride Sesquihydrate and Beta-Cyclodextrin 3 g of beta-cyclodextrin was added in 60 mL of water, the reaction mass was heated to 85° C. to get the clear solution, to this solution 1 g of pitolisant hydrochloride was added, stirred to get clear solution. The solution was distilled under vacuum at 70-80° C.

Example 14. General Process for Preparing Solid Dispersion without Isolating Pitolisant Hydrochloride To 100 g of N,N-dimethylacetamide, 12 g of potassium tertiary butoxide was added under stirring. To the reaction mass 3-(piperidin-1-yl)propan-1-ol was added to the reaction mass with heating was heated to 50-60° C. and stirred for 60 minutes. The reaction mass was cooled to room temperature and stirred for 15 minutes. To the reaction mass a solution of 3-(4-chlorophenyl)propylmethane sulfonate was dissolved in N,N-dimethylacetamide was added and stirred for 12-14 hours. The reaction mass was cooled to 0-5° C., sodium chloride solution was added, stirred and the reaction mass temperature was raised to room temperature. To the reaction mass, toluene was added and layer was separated. To the aqueous layer toluene was added, stirred and layers were separated. To the combined organic layer dilute hydrochloric acid was added, stirred and layers were separated. The aqueous layer was extracted with dichloromethane, layers were separated, and the organic layer was treated with carbon, stirred filtered and bed was washed with methylene dichloride. To the filtrate sodium sulphate was added, stirred, filtered and the filtrate was distilled under vacuum. To the residue, isopropanolic hydrochloride was added and distilled under vacuum to the syrup. To the syrup isopropanol was added and distilled to get the syrup. To the syrup corresponding solvent was added and stirred, to the solution one or more pharmaceutically acceptable excipients was added and heated (if required) to the get the clear solution. The obtained solution was spray dried or distilled to obtain the corresponding solid dispersion comprising pitolisant hydrochloride and one or more pharmaceutically acceptable excipients.

Example 15. Process for Preparing Solid Dispersion without Isolating Pitolisant Hydrochloride To 100 g of N,N-dimethylacetamide, 12 g of potassium tertiary butoxide was added under stirring. To the reaction mass 3-(piperidin-1-yl)propan-1-ol was added under stirring and the reaction mass was heated to 50-60° C. and stirred for 60 minutes. The reaction mass cooled to room temperature and stirred for 15 minutes. To the reaction mass a solution of 3-(4-chlorophenyl)propyl methanesulfonate in N,N-dimethylacetamide was added and stirred for 12-14 hours. The reaction mass was cooled to 0-5° C., sodium chloride solution was added, stirred and the reaction mass temperature was raised to room temperature. The reaction mass was extracted with toluene and the organic layer was distilled completely. To the residue acetone was added stirred, fumaric acid (1 eq) was added and stirred for 2 hours. The obtained solid was filtered, washed with acetone and suck dried.

To the pitolisant fumaric acid salt, aqueous sodium hydroxide solution was added and stirred. The solution was extracted with toluene and layers were separated. To the combined organic layer dilute hydrochloric acid was added, stirred and layers were separated. The aqueous layer was extracted with dichloromethane, layers were separated, and the organic layer was treated with carbon, stirred, filtered and the bed was washed with methylene dichloride. To the filtrate sodium sulphate was added, stirred, filtered and the filtrate was distilled under vacuum. To the residue, isopropanolic hydrochloride was added stirred for 2 hours and distilled under vacuum to the syrup. To the syrup isopropanol was added and distilled to get the syrup.

Example 16. Process for Preparing Solid Dispersion without Isolating Pitolisant Hydrochloride To 100 g of N,N-dimethylacetamide, 12 g of potassium tertiary butoxide was added under stirring. To the reaction mass 3-(piperidin-1-yl)propan-1-ol was added under stirring and the reaction mass was heated to 50-60° C. and stirred for 60 minutes. The reaction mass was cooled to room temperature and stirred for 15 minutes. To the reaction mass a solution of 3-(4-chlorophenyl) propyl methanesulfonate dissolved in N,N-dimethylacetamide was added and stirred for 12-14 hours. The reaction mass was cooled to 0-5° C., sodium chloride solution was added, stirred and the reaction mass temperature was raised to room temperature. To the reaction mass toluene was added and layer was separated. To the aqueous layer toluene was added, stirred and layers were separated. To the combined organic layer fumaric acid was added, stirred and layers were separated. The aqueous layer was extracted with dichloromethane, layers were separated, and the organic layer was treated with carbon, stirred, filtered and bed was washed with methylene dichloride. To the filtrate sodium sulphate was added, stirred, filtered and the filtrate was distilled under vacuum. To the residue, isopropanolic hydrochloride and distilled under vacuum to obtain the syrup. To the syrup isopropanol was added and distilled to obtain the syrupy mass.

This syrupy mass obtained from above example was used for the preparation of solid dispersions, cocrystals and polymorphs and hydrate forms of pitolisant hydrochloride as disclosed herein.

Example 17. Process for Preparing Solid Dispersion of Pitolisant Hydrochloride and Beta-Cyclodextrin without Isolating Pitolisant Hydrochloride To 100 g of N,N-dimethylacetamide, 12 g of potassium tertiary butoxide was added under stirring. To the reaction mass 3-(piperidin-1-yl)propan-1-ol was added under stirring and the reaction mass was heated to 50-60° C. and stirred for 60 minutes. The reaction mass was cooled to room temperature and stirred for 15 minutes. The reaction mass was cooled to 10-20° C. and a solution of 3-(4-chlorophenyl) propyl methanesulfonate dissolved in N,N-dimethylacetamide was added and stirred for 5-6 hours at room temperature. After completion of the reaction the reaction mass was cooled to 5-15° C., sodium chloride solution was added and the reaction mass was extracted with toluene. The organic layer was washed with water and extracted with hydrochloric acid solution. The aqueous layer was extracted with methylene dichloride and layers were separated. The organic layer was basified with aqueous sodium hydroxide solution and the organic layer was washed with water. The organic layer was concentrated, methanol and acetone (1:3) was added to the viscous mass followed by addition of oxalic acid dihydrate (1 eq). The reaction mass was heated to get clear solution, cooled to room temperature and stirred for 7-10 hours. The reaction mass was further cooled to 0-10° C. and stirred for 1-2 hours. The obtained crystalline oxalate salt was filtered, washed with methanol and acetone mixture and dried under vacuum at 40° C.

To 20 g of pitolisant oxalate salt, toluene (5V) was added and stirred. To the reaction mass water (8V) was added and the pH was adjusted to 12-14 with 20% sodium hydroxide solution. The reaction mass was stirred and separated layers. The aqueous layer was extracted with toluene and the combined organic layers washed with water. The pH of the organic layer was adjusted to 1-2 with 1:1 hydrochloric acid solution. The layers were separated, the organic layer was extracted with 1:1 hydrochloric acid solution. The combined aqueous layer was extracted with methylene dichloride. The organic layer was concentrated to obtain syrupy mass of pitolisant hydrochloride.

To the syrupy mass water was added heated to 75-85° C., beta-cyclodextrin (1:3 with respect to pitolisant hydrochloride) was added under heating, stirred the reaction mass to obtain clear solution. The clear solution was spray dried.

| Spray type: | Open loop |
|---|---|
| Feeding rate: | 20 mL/min |
| Chamber temperature: | 100-105° C. |
| Nitrogen flow rate: | 3.54 kg/cm$^2$ |
| Vacuum: | −34 mmwc |
| Agitator speed: | 7 rpm |

To 20 g of pitolisant oxalate salt, water was added (20V) and the pH of the reaction mass was adjusted to 12-14 with 20% sodium hydroxide solution. To the reaction mass methylene dichloride was added, stirred and layers were separated. The aqueous layer was extracted with methylene dichloride and the combined organic layers were washed with water. The organic layer was concentrated and the obtained residue diluted with methylene dichloride. The pH of the reaction mass was adjusted to 1-2 with 1:1 hydrochloric acid solution, stirred and concentrated.

To the syrupy mass water was added heated to 75-85° C., β-cyclodextrin (1:3 with respect to pitolisant hydrochloride) was added under heating, stirred the reaction mass to obtain clear solution. The clear solution was spray dried.

| Spray type: | Open loop |
|---|---|
| Feeding rate: | 20 mL/min |
| Chamber temperature: | 100-105° C. |
| Nitrogen flow rate: | 3.54 kg/cm$^2$ |
| Vacuum: | −34 mmwc |
| Agitator speed: | 7 rpm |

Example 18. Process for Preparing Solid Dispersion Comprising Pitolisant Hydrochloride and Copovidone without Isolating Pitolisant Hydrochloride To 100 g of N,N-dimethylacetamide, 12 g of potassium tertiary butoxide was added under stirring. To the reaction mass 3-(piperidin-1-yl)propan-1-ol was added under stirring and the reaction mass was heated to 50-60° C. and stirred for 60 minutes. The reaction mass was cooled to room temperature and stirred for 15 minutes. The reaction mass was cooled to 10-20° C. and a solution of 3-(4-chlorophenyl) propyl methanesulfonate dissolved in N,N-dimethylacetamide was added and stirred for 5-6 hours at room temperature. After completion of the reaction the reaction mass was cooled to 5-15° C., sodium chloride solution was added and the reaction mass was extracted with toluene. The organic layer was washed with water and extracted with hydrochloric acid solution. To the aqueous layer was extracted with methylene dichloride and layers were separated. The organic layer was basified with aqueous sodium hydroxide solution and the organic layer was washed with water. The organic layer was concentrated, methanol and acetone (1:3) was added to the viscous mass followed by addition of oxalic acid dihydrate. The reaction mass was heated to get clear solution, cooled to room temperature and stirred for 7-10 hours. The reaction mass was further cooled to 0-10° C. and stirred for 1-2 hours. The obtained crystalline oxalate salt was filtered, washed with methanol and acetone mixture and dried under vacuum at 40° C.

To 20 g of pitolisant oxalate salt toluene (5V) was added and stirred. To the reaction mass water (8V) was added and the pH was adjusted to 12-14 with 20% sodium hydroxide solution. The reaction mass was stirred and separated layers. The aqueous layer was extracted with toluene and the combined organic layers were washed with water. The pH of the organic layer was adjusted to 1-2 with 1:1 hydrochloric acid solution. The layers was separated, the organic layer was extracted with 1:1 hydrochloric acid solution. The combined aqueous layer was extracted with methylene dichloride. The organic layer was concentrated to obtain syrupy mass of pitolisant hydrochloride.

To the syrupy mass isopropanol and copovidone (1:5 with respect to pitolisant hydrochloride) was added under heating, stirred the reaction mass to obtain clear solution. The clear solution was spray dried.

| Spray type: | Close loop |
|---|---|
| Feeding rate: | 20 mL/min |
| Chamber temperature: | 78-83° C. |
| Nitrogen flow rate: | 3.54 kg/cm$^2$ |
| Vacuum: | −34 mmwc |
| Agitator speed: | 7 rpm |

To 20 g of pitolisant oxalate salt, water as added (20V) and the pH of the reaction mass was adjusted to 12-14 with 20% sodium hydroxide solution. To the reaction mass methylene dichloride was added, stirred and layers were separated. The aqueous layer was extracted with methylene dichloride and the combined organic layers were washed with water. The organic layer was concentrated and the obtained residue diluted with methylene dichloride. The pH of the reaction mass was adjusted to 1-2 with 1:1 hydrochloric acid solution, stirred and concentrated.

To the syrupy mass isopropanol and copovidone (1:5 with respect to pitolisant hydrochloride) was added under heating, stirred the reaction mass to obtain clear solution. The clear solution was spray dried to obtain amorphous solid dispersion.

| Spray type: | Close loop |
|---|---|
| Feeding rate: | 20 mL/min |
| Chamber temperature: | 78-83° C. |
| Nitrogen flow rate: | 3.54 kg/cm$^2$ |
| Vacuum: | −34 mmwc |
| Agitator speed: | 7 rpm |

Example 19. Process for Preparing Solid Dispersion Comprising Pitolisant Hydrochloride and Povidone 20 g of pitolisant hydrochloride syrup was dissolved in 200 mL isopropanol, to this solution 6 g of povidone was added, stirred to get clear solution. The solution was filtered and the filtrate was spray dried to obtain amorphous solid dispersion shown in FIG. 2.

| Spray type: | Closed loop |
|---|---|
| Spray rate: | 5 mL/min |
| Chamber temperature: | 60-65° C. |

1 g of pitolisant hydrochloride syrup was dissolved in 5 mL isopropanol, to this solution 0.3 g of povidone was added, stirred to get clear solution. The solution was distilled under vacuum at 50-60° C.

Example 20. Solid Dispersion Comprising Pitolisant Hydrochloride and Copovidone 1 g of pitolisant hydrochloride syrup was dissolved in 50 mL isopropanol, to this solution 5 g of copovidone was added, stirred to get clear solution. The solution was filtered and the filtrate was distilled to obtain amorphous solid dispersion.

5 g of pitolisant hydrochloride syrup was dissolved in 500 mL isopropanol, to this solution 25 g of copovidone was added, stirred to get clear solution. The solution was spray dried to obtain amorphous solid dispersion.

Example 21. Solid Dispersion Comprising Pitolisant Hydrochloride and Beta-Cyclodextrin 75 g of beta-cyclodextrin was added to 1250 mL of water and the mixture was heated to 85° C. to get clear solution, to this solution 25 g of pitolisant hydrochloride syrup was added, stirred to get clear solution. The solution was filtered and the filtrate was spray dried to obtain amorphous solid dispersion.

| | |
|---|---|
| Spray type: | Open loop |
| Spray rate: | 5 mL/min |
| Chamber temperature: | 90-95° C. |

Example 22. Pitolisant Hydrochloride Sesquihydrate

To 10 g of pitolisant obtained according to Raga's Example 1, 50 mL of dichloromethane was added under stirring. The reaction mass was heated to reflux temperature and stirred. To the reaction mass aqueous solution of hydrochloride was added, pH was adjusted to 3-4 and stirred. The reaction mass was heated to get the clear solution, treated with carbon and stirred. The reaction mass was filtered at hot condition and 100 mL of water was added to the filtrate and stirred at reflux temperature. The reaction mass was transferred to ice bath and cooled to 5° C. and transferred to refrigerator for 12 hours. The obtained solid is washed with dichloromethane followed by water, dried in air to obtain pitolisant hydrochloride sesquihydrate with a chemical purity of 99.5% and a moisture content 7.7%.

Example 23. Pitolisant Hydrochloride Dihydrate

To 10 g of crude 1-{3-[3-(4-chlorophenyl)propoxy] propyl}piperidine obtained according to Raga's Example 1, 50 mL of acetone was added under stirring. The reaction mass was heated to reflux temperature and stirred. To the reaction mass aqueous solution of hydrochloride was added, pH was adjusted to 3-4 and stirred. The reaction mass was heated to get the clear solution, treated with carbon and stirred. The reaction mass filtered at hot condition and 120 mL of water was added to the filtrate and stirred at reflux temperature. The reaction mass was transferred to ice bath and cooled to 5° C., stirred and transferred to refrigerator for 12 hours. The obtained solid was washed with dichloromethane and water, dried naturally to obtain pitolisant hydrochloride dihydrate with a chemical purity of 99.5% and a moisture content 9.8%.

Example 24. Preparation of Pitolisant Hydrochloride Hemipentahydrate

To 10 g of 1-{3-[3-(4-chlorophenyl)propoxy] propyl}piperidine obtained according to Raga's Example 1, 50 mL of acetone was added under stirring. The reaction mass was heated to reflux temperature and stirred. To the reaction mass aqueous solution of hydrochloride was added, pH was adjusted to 3-4 and stirred. The reaction mass was heated to get clear solution, treated with carbon and stirred. The reaction mass was filtered at hot condition, 140 mL of water was added to the filtrate and stirred at reflux temperature. The reaction mass was transferred to ice bath and cooled to 5° C., stirred for 10 hours and transferred to refrigerator for 15 hours. The obtained solid is washed with acetone and water, dried naturally to obtain pitolisant hydrochloride hemipentahydrate with a chemical purity of 99.6% and a moisture content 12.3%.

Example-25: Pitolisant Hydrochloride Trihydrate

To 10 g of 1-{3-[3-(4-chlorophenyl)propoxy] propyl}piperidine obtained according to Raga's Example 1, 50 mL of isopropanol was added under stirring. The reaction mass was heated to reflux temperature and stirred. To the reaction mass aqueous solution of hydrochloride was added, pH was adjusted to 3-4 and stirred. The reaction mass was heated to get the clear solution, treated with carbon and stirred. The reaction mass was filtered at hot condition and 160 mL of water was added to the filtrate and stirred at reflux temperature. The reaction mass was transferred to ice bath and cooled to 5° C., stirred for 10 hours and transferred to refrigerator for 20 hours. The obtained solid was washed with isopropanol and water, dried naturally to obtain pitolisant hydrochloride trihydrate with a chemical purity of 99.4% and a moisture content 14.4%.

Example 26. Pitolisant Hydrochloride Pentahydrate

To 10 g of crude 1-{3-[3-(4-chlorophenyl)propoxy] propyl}piperidine obtained according to Raga's Example 1, 50 mL of ethylacetate was added under stirring. The reaction mass was heated to reflux temperature and stirred. To the reaction mass aqueous solution of hydrochloride was added, pH was adjusted to 3-4 and stirred. The reaction mass was heated to get the clear solution, treated with carbon and stirred. The reaction mass filtered at hot condition and 180 mL of water was added to the filtrate and stirred at reflux temperature. The reaction mass was transferred to ice bath and cooled to 5° C., stirred for 10 hours and transferred to refrigerator for 24 hours. The obtained solid is washed with ethylacetate and water, dried naturally to obtain pitolisant hydrochloride pentahydrate with a chemical purity of 99.5% and a moisture content 21.2%.

Example 27. Pitolisant Hydrochloride Trihydrate

To 10 g of crude 1-{3-[3-(4-chlorophenyl)propoxy] propyl}piperidine obtained according to Raga's Example 1, 50 mL of water was added under stirring. The reaction mass was heated to reflux temperature and stirred. To the reaction mass aqueous solution of hydrochloride was added, pH was adjusted to 3-4 and stirred. The reaction mass was heated to get the clear solution, treated with carbon and stirred. The reaction mass was filtered at hot condition and 100 mL of water was added to the filtrate and stirred at reflux temperature. To the reaction mass water cyclohexane was added and stirred for 6 hours to get the precipitate. The organic layer was separated reaction mass cooled rapidly to 3° C. in ice bath and stirred for 10 hours and transferred to refrigerator for 18 hours. The obtained solid was dried naturally to obtain pitolisant hydrochloride trihydrate with a chemical purity of 99.6% and a moisture content 14.4%.

Example 28. Pitolisant Hydrochloride Pentahydrate

To 10 g of crude 1-{3-[3-(4-chlorophenyl)propoxy]propyl}piperidine obtained according to Raga's Example 1, 50 mL of water was added under stirring. The reaction mass was heated to reflux temperature and stirred. To the reaction mass aqueous solution of hydrochloride was added, pH was adjusted to 3-4 and stirred. The reaction mass was heated to get the clear solution, treated with carbon and stirred. The reaction mass filtered at hot condition and 150 mL of water was added to the filtrate and stirred at reflux temperature. To the reaction mass water cyclohexane was added and stirred for 6 hours to get the precipitate. The organic layer was separated reaction mass cooled rapidly to 3° C. in ice bath and stirred for 10 hours and transferred to refrigerator for 24 hours. The obtained solid was dried naturally to obtain pitolisant hydrochloride pentahydrate with a chemical purity of 99.6% and a moisture content 21.2%.

Example 29. Pitolisant Hydrochloride Dihydrate

To a crude 10 g of 1-{3-[3-(4-chlorophenyl)propoxy]propyl}piperidine obtained according to Raga's Example 1, 50 mL of water was added under stirring. The reaction mass was heated to reflux temperature and stirred. To the reaction mass aqueous solution of hydrochloride was added, pH was adjusted to 3-4 and stirred. The reaction mass was heated to get the clear solution, treated with carbon and stirred. The reaction mass filtered at hot condition and 75 mL of water was added to the filtrate and stirred at reflux temperature. To the reaction mass water cyclohexane was added and stirred for 6 hours to get the precipitate. The organic layer was separated reaction mass cooled rapidly to 3° C. in ice bath and stirred for 10 hours and transferred to refrigerator for 12 hours. The obtained solid was dried naturally to obtain pitolisant hydrochloride dihydrate with a chemical purity of 99.6% and a moisture content 9.8%.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims, while the description, abstract and drawings are not to be used to limit the scope of the invention. The invention is specifically intended to be as broad as the claims below and their equivalents.

Disclosed Aspects

Aspect 1. A solid dispersion comprising pitolisant hydrochloride and one or more pharmaceutically acceptable excipients.

Aspect 2. The solid dispersion of Aspect 2, wherein the one or more pharmaceutically acceptable excipients is selected from a polyvinyl pyrrolidone, a polyvinylpyrrolidone vinylacetate, a polyvinylacetal diethylaminoacetate, a polyvinyl acetate phthalate, a polyoxyethylene sorbitan fatty acid ester, a polyoxyethylene-polyoxypropylene copolymer, a polyoxyethylene stearate, a polyethylene glycol monomethyl ether, colloidal silicon dioxide, a polyethylene glycol, a polyoxylglyceride, a methylcellulose, a methacrylic acid copolymer, a hydroxypropylmethyl cellulose, a hydroxypropyl cellulose, a hydroxypropylmethyl cellulose phthalate, a hydroxypropylmethyl cellulose acetate succinate, a hydroxypropylmethyl cellulose, a hydroxypropyl cellulose SSL, hydroxypropyl cellulose SL, hydroxypropyl cellulose L, hydroxyethyl cellulose, a polyvinyl caprolactam-polyvinyl acetate-polyethylene glycol graft copolymer, a polyoxylglyceride, an ethyl cellulose, a D-alpha-tocopheryl polyethylene glycol 1000 succinate, a cellulose acetate phthalate, a carboxymethylethyl cellulose and the like, a cyclodextrin, a substituted cyclodextrin or a pharmaceutically acceptable salt thereof (e.g., a HP—β-CD, a sodium salt of SBE(6-7)-β-CD or a sodium salt of sugammadex, and the like), a gelatin, a hypromellose phthalate, a sugar, a polyhydric alcohol and the like, a water soluble sugar excipient, a polyethylene oxide, a polyoxyethylene derivative, a polyvinyl alcohol, a propylene glycol derivative, and a combination thereof.

Aspect 3. The solid dispersion of any one of Aspects 1-2, wherein the solid dispersion comprises an amorphous solid dispersion comprising pitolisant hydrochloride and β-cyclodextrin having a powder X-ray diffraction pattern substantially as depicted in FIG. 1.

Aspect 4. The solid dispersion of any one of Aspects 1-2, wherein the solid dispersion comprises an amorphous solid dispersion comprising pitolisant hydrochloride and povidone having a powder X-ray diffraction pattern substantially as depicted in FIG. 2.

Aspect 5. The solid dispersion of any one of Aspects 1-2, wherein the amorphous solid dispersion comprising pitolisant hydrochloride and copovidone having a powder X-ray diffraction pattern substantially as depicted in FIG. 3.

Aspect 6. The solid dispersion of any one of Aspects 1-5, obtained by a process, which comprises: a) providing a solution of pitolisant hydrochloride in a solvent; b) adding one or more pharmaceutically acceptable excipients to the solvent; and c) removing the solvent from the reaction mass.

Aspect 7. The solid dispersion of Aspect 6, wherein the removal of solvent from the reaction is carried out by at least one of evaporation, spray drying, and freeze drying.

Aspect 8. A process for the preparation a solid dispersion comprising pitolisant hydrochloride and one more pharmaceutically acceptable excipients, said process comprising: a. providing pitolisant first salt in a solvent; b. neutralizing the first pitolisant salt with a base to obtain pitolisant; c. treating the pitolisant with hydrochloride to obtain a pitolisant hydrochloride solution; d. adding one or more pharmaceutically acceptable excipients; e. removing the solvent from the reaction mass; and f. isolating a solid dispersion comprising pitolisant hydrochloride and the one or more pharmaceutical acceptable excipients; wherein the reaction is carried out without isolation of pitolisant hydrochloride salt.

Aspect 9. The process of Aspect 8, wherein the pitolisant first salt is an acid addition salt where the acid is selected from hydrobromic acid, hydroiodic acid, oxalic acid, fumaric acid, maleic acid, succinic acid, acetic acid, adipic acid, ascorbic acid, aspartic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutamic acid, glutaric acid, glycerophosphoric acid, glycolic acid, hippuric acid, isobutyric acid, lactic acid, lactobionic acid, lauric acid, maleic acid, malic acid, malonic acid, mandelic acid, naphthalene-1,5-disulfonic acid, naphthalene-2-sulfonic acid, nicotinic acid, nitric acid, oleic acid, oxalic acid, palmitic acid, pamoic acid, pyroglutamic acid, salicylic acid, sebacic acid, stearic acid, succinic acid, tartaric acid, thiocyanic acid, undecylenic acid, aminocaproic acid, caprilic acid, alpha lipoic acid, R-lipoic acid, myristic acid, myristoleic acid, palmitoleic acid, elaidic acid, linoleic acid, linolenic acid, linolelaidic acid, arachidonic acid, and a combination thereof.

Aspect 10. The process of any one of Aspects 8-9, wherein the base in step b) comprises an inorganic base, an organic base, or a combination thereof selected from sodium hydroxide, potassium hydroxide, lithium hydroxide, sodium carbonate, potassium carbonate, lithium carbonate, sodium bicarbonate, potassium bicarbonate, lithium bicarbonate, trimethylamine, and diisopropylamine, and a combination thereof.

Aspect 11. A process for preparing pitolisant or a pharmaceutically acceptable salt thereof, comprising:
a) reacting 3-(piperidin-1-yl)propan-1-ol

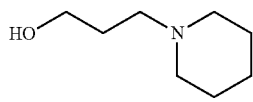

with Formula-(III);

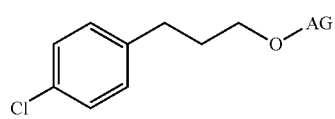
Formula-(III)

in the presence of a solvent and a base to obtain pitolisant;
b) treating pitolisant with a pharmaceutically acceptable acid; and
c) isolating the pitolisant pharmaceutically acceptable salt wherein the base is not sodium hydride; and
wherein AG is selected from an alkylsulfonate, an arylsulfonate, an alkyl ester, and an aryl ester.

Aspect 12. The process of Aspect 11, wherein the base used in step a) is organic or inorganic base which is selected from sodium hydroxide, sodium carbonate, sodium bicarbonate, sodium methoxide, potassium hydroxide, potassium carbonate, potassium bicarbonate, potassium tertiary-butoxide, triethylamine, t-butylamine, trimethylamine and N,N-diisopropylamine, and a combination thereof.

Aspect 13. The process of any one of Aspects 11-12, wherein the solvent of step a) is selected from N,N-dimethylformamide, N,N-dimethylacetamide, dimethylsulfoxide, 1-methyl-2-pyrrolidone, 1-methyl-2-piperidone, 1,3-dimethyl-2-imidazolidinone, acetonitrile, acetone, dichloromethane, ethyl acetate, tetrahydrofuran, acetone, and a combination thereof.

Aspect 14. Pitolisant hydrochloride sesquihydrate.

Aspect 15. The pitolisant hydrochloride sesquihydrate of Aspect 14 having PXRD peaks at 5.3, 7.3, 10.0, 11.8, and 26.1±0.2° two-theta.

Aspect 16. Crystalline pitolisant oxalate having PXRD peaks at 7.4, 14.8, 21.8, 22.3, and 29.8±0.2° two-theta.

Aspect 17. A process for preparing pitolisant hydrochloride, which comprises converting the crystalline pitolisant oxalate of Aspect 16 to pitolisant hydrochloride, its hydrates, and solid-state forms thereof.

Aspect 18. A process for preparing pitolisant or a pharmaceutically acceptable salt thereof, which comprises the preparation of 3-(4-chlorophenyl)-propanol of Formula-(V), said process comprising:

a) providing 3-(4-chlorophenyl)-propionic acid of Formula-(IV);

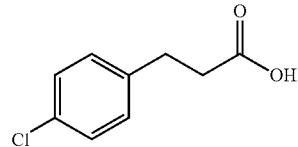
Formula-(IV)

b) converting 3-(4-chlorophenyl)-propionic acid of Formula-(IV) to its acid chloride of Formula-(VI) or acid anhydride of Formula-(VIA);

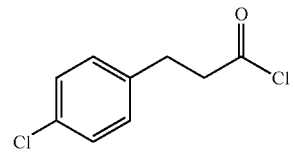
Formula-(VI)

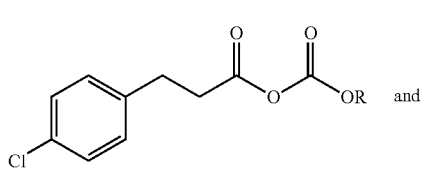
Formula-(VIA)

and c) reducing acid chloride of Formula-(VI) or acid anhydride Formula-(VIA), where R is an alkyl or a phenyl, to obtain 3-(4-chlorophenyl)-propanol of Formula-(V)

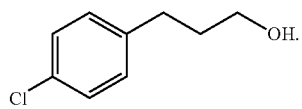
Formula-(V)

Aspect 19. The process of Aspect 18, further comprising reacting 3-(4-chlorophenyl)-propanol of Formula-(V) with Formula-(III)

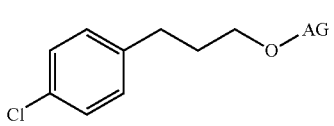
Formula-(III)

to obtain pitolisant;
wherein AG is selected from an alkylsulfonate, an arylsulfonate, an alkyl ester, and an aryl ester.

Aspect 20. Pitolisant, its pharmaceutically acceptable salt, hydrate, and solid-state form thereof having a chemical purity not less than 98% and substantially free of impurities selected from Formula-(VA), deschloro mesyl compound of Formula-(IIIA), and deschloro pitolisant of Formula-(IA)

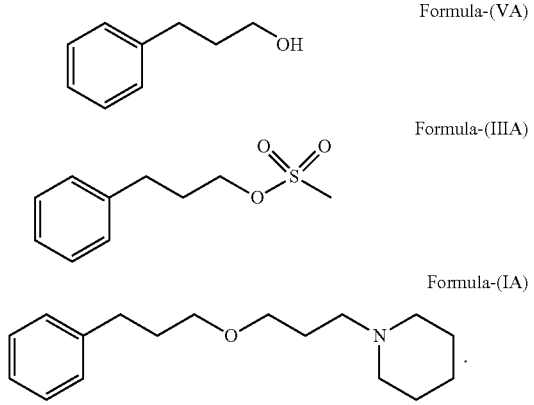

The subject matter of Indian Patent Application Nos. 202141025328 (filed on Jun. 7, 2021), 202141035609 (filed on Aug. 6, 2021), 202141046743 (filed on Oct. 13, 2021), and 202241009416 (filed on Feb. 22, 2022) is incorporated by reference in its entirety. Additionally, the subject matter of the documents cited herein is incorporated by reference in their entirety to the extent necessary. If there is a difference in meaning between the incorporated terms and the terms disclosed herein, the meaning of the terms disclosed herein will control.

CITED INFORMATION

EFSA Panel et al., Safety of low-substituted hydroxypropyl cellulose (L-HPC) to be used as a food additive in food supplements in tablet form, EFSA Journal (2018) 16(1): 5062 ("EFSA Panel").

European Patent Application Publication No. EP 3 239 138 A1, Hydrogen fumarate salt of 1-[3-[3-(4-chlorophenyl)propoxy]propyl]-piperidine, published on Nov. 1, 2017 to Stefinovic et al. of Sandoz AG ("Sefinovic").

Greene et al., Protective Groups in Organic Synthesis (2nd ed., John Wiley & Sons, Inc.) (1991), pages 87-118 ("Greene").

Handbook of Pharmaceutical Excipients, 6th Ed., Eds. Rowe et al. (2009) ("Handbook").

International Publication No. WO 2007/006708 A1, Process for preparing 1-[3-[3-chlorophenyl)propoxy]propyl]-piperidine, published on Jan. 18, 2007, to Sallarés et al. of Ferrer International, S.A. ("Sallarés").

International Publication No. WO 2021/023634 A1, Process for the synthesis of pitolisant HCl, published on Feb. 11, 2021. to Colombano et al. of Procos S.P.A ("Colombano").

Meier et al., *Influence of imidazole replacement in different structural classes of histamine H3-receptor antagonists*, Eur. J. Pharm. Sci. (2001) 13(3): 249-259 ("Meier").

Remington's Pharmaceutical Sciences (17th ed., Mack Publishing Company) and Remington: The Science and Practice of Pharmacy (21st ed., Lippincott Williams & Wilkins), collectively "Remington's."

Sarode et al., Low-Viscosity Hydropropylcellulose (HPC) Grades SL and SSL: Versatile Pharmaceutical Polymers for Dissolution Enhancement, Controlled Release, and Pharmaceutical Processing, AAPS PharmSciTech (2013) 14(1): 151-159 ("Sarode").

U.S. Patent Application Publication No. US 2014/0377185 A9, Stabilized formulations containing iodinated contrast agents and cyclodextrins, published on Dec. 25, 2014 to Mosher et al. of Verrow Pharmaceuticals, Inc. ("Mosher")

U.S. Pat. No. 6,949,527 B2, 6-mercapto-cyclodextrin derivatives: reversal agents for drug-induced neuromuscular block, issued on Sep. 27, 2005 to Zhang et al. of Akzo Nobel N.V. ("Zhang").

U.S. Pat. No. 7,910,605 B2, Non-imidazole alkylamines as histamine H3-receptor ligands and their therapeutic applications, issued on Mar. 2, 2011 to Schwartz et al. of Societe Civile Bioproject ("Schwartz").

U.S. Pat. No. 8,207,197 B2, Monohydrochloride salt of 1-[3-[3-(4-chlorophenyl)propoxy]propyl]-piperidine, issued on Jun. 26, 2012 to Raga et al. of Bioproject ("Raga").

U.S. Pat. No. 11,324,692 B2, Method to prepare pharmaceutical compositions of sugammadex, issued on May 10, 2022 to Coello et al. of Galenicum Health S.L.U. ("Coello").

WAKIX® (pitolisant) tablets prescribing information, as of Oct. 13, 2020 ("WAKIX® Label").

All cited information is hereby incorporated by reference to the same extent as if each reference were individually and specifically indicated to be incorporated by reference and were set forth in its entirety herein. If there is a difference in meaning between the information of the cited information terms and the terms disclosed herein, the meaning of the terms disclosed herein will control.

The use of the terms "a," "an," "the," "one or more," and "at least one" and similar referents in the context of describing the invention (especially in the context of the following claims) are to be construed to cover both the singular and the plural, unless otherwise indicated herein or clearly contradicted by context. The use of the terms "at least one" and "one or more" followed by a list of one or more items (for example, "at least one of A and B" or "one or more of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. As used herein, the term "exemplary" indicates an example thereof and does not suggest a best or optimal of the recited item. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The expression "amorphous solid dispersion," as used herein, means that the dispersion comprising the solid dispersion having 100% amorphous or at least 98% amorphous or at least 95% amorphous or at least 90% amorphous or at least 85% amorphous or at least 80% amorphous in nature.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. For instance, the expression "comprising" may be replaced by the expression "consist of" or "consisting of," as understood from information disclosed herein.

The invention claimed is:

1. A process for preparing pitolisant or a pharmaceutically acceptable salt and its solid state forms thereof, comprising:
   a) providing 3-(4-chlorophenyl)-propionic acid of Formula-(IV);

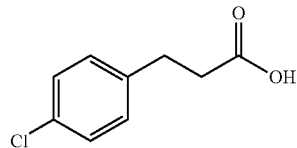

Formula-(IV)

b) converting 3-(4-chlorophenyl)-propionic acid of Formula-(IV) to its acid chloride of Formula-(VI) or acid anhydride of Formula-(VIA);

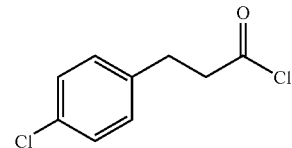

Formula-(VI)

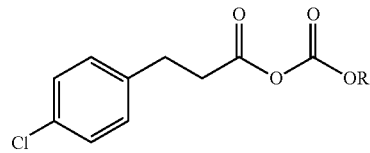

Formula-(VIA)

c) reducing acid chloride of Formula-(VI) or acid anhydride Formula-(VIA), where R is an alkyl or a phenyl, to obtain 3-(4-chlorophenyl)-propanol of Formula-(V);

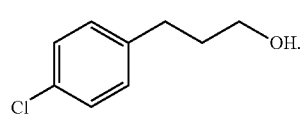

Formula-(V)

d) treating compound of formula (V) with activating group to obtain a compound of formula (III);

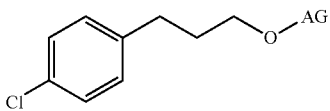

Formula-(III)

e) reacting 3-(piperidin-1-yl)propan-1-ol

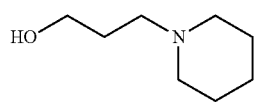

with Formula-(III);

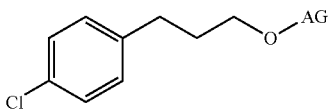

Formula-(III)

in the presence of a solvent and a base to obtain pitolisant; wherein the AG is an activating group;
   f) optionally treating pitolisant with an acid to form pitolisant first salt; and
   g) converting pitolisant or pitolisant first salt to pharmaceutically acceptable salt or solid state forms of pitolisant;
   with the proviso that the base in step e) is not sodium hydride; and
   wherein AG is selected from a methyl sulfonate, an ethylsulfonate, a phenylsulfonate, a tolylsulfonate, a p-nitrophenyl sulfonate, a benzyl sulfonate, a trifluoromethylacyl ester, a trichloromethylacyl ester, a phenylacyl ester, a p-nitro-phenylacyl ester, and a p-chloro-phenylacyl ester.

2. The process of claim 1, wherein the 3-(4-chlorophenyl)-propionic acid of Formula (IV) in step a) is dissolved in solvent selected from dichloromethane, dichloroethane, tetrahydrofuran, toluene, dioxane, N,N-dimethylformamide, N,N-dimethylacetamide, dimethylsulfoxide, 1-methyl-2-pyrrolidone, 1-methyl-2-piperidone, 1,3-dimethyl-2-imidazolidinone, acetonitrile, acetone, ethyl acetate, methanol, ethanol, isopropanol, n-butanol and combination thereof.

3. The process of claim 1, wherein the conversion of 3-(4-chlorophenyl)-propionic acid of Formula-(IV) to its acid chloride of Formula-(VI) is carried out in presence of a chlorinating agent selected from phosgene, diphosgene, triphosgene, thionyl chloride, oxalyl chloride and phosphorus oxychloride.

4. The process of claim 1, wherein 3-(4-chlorophenyl)-propionic acid of Formula-(IV) to its acid anhydride of Formula-(VIA) is carried out in presence of a haloformate selected from methylchloroformate, ethylchloroformate, isopropyl chloroformate, isobutyl chloroformate, and phenyl chloroformate.

5. The process of claim 1, wherein the reaction of step b) is carried out in presence of solvent selected from dichloromethane, dichloroethane, tetrahydrofuran, toluene, dioxane, N,N-dimethylformamide, N,N-dimethylacetamide, dimethylsulfoxide, 1-methyl-2-pyrrolidone, 1-methyl-2-piperidone, 1,3-dimethyl-2-imidazolidinone, acetonitrile, acetone, ethyl acetate, methanol, ethanol isopropanol, n-butanol and a combination thereof.

6. The process of claim 1, wherein the reduction reaction of step c) is carried out in presence of a borohydride selected from lithium borohydride, sodium borohydride, potassium borohydride, sodium cyanoborohydride, lithium triethyl borohydride, and a combination thereof.

7. The process of claim 1, wherein the base used in step e) is organic or inorganic base which is selected from sodium hydroxide, sodium carbonate, sodium bicarbonate, sodium methoxide, potassium hydroxide, potassium carbonate, potassium bicarbonate, potassium tertiary-butoxide, triethylamine, t-butylamine, trimethylamine and N, N-diisopropylamine, and a combination thereof.

8. The process of claim 1, wherein the solvent is polar aprotic solvent.

9. The process of claim 1, wherein the solvent of step e) is selected from N,N-dimethylformamide, N,N-dimethylacetamide, dimethylsulfoxide, 1-methyl-2-pyrrolidone, 1-methyl-2-piperidone, 1,3-dimethyl-2-imidazolidinone, acetonitrile, acetone, dichloromethane, ethyl acetate, tetrahydrofuran, acetone, and a combination thereof.

10. The process of claim 1, wherein the step e) reaction is carried out at temperature in the range from about 0° C. to about the reflux temperature of solvent.

11. The process of claim 1, wherein the pitolisant first salt is an acid addition salt where the acid is selected from hydrobromic acid, hydroiodic acid, oxalic acid, fumaric acid, maleic acid, succinic acid, acetic acid, adipic acid, ascorbic acid, aspartic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutamic acid, glutaric acid, glycerophosphoric acid, glycolic acid, hippuric acid, isobutyric acid, lactic acid, lactobionic acid, lauric acid, maleic acid, malic acid, malonic acid, mandelic acid, naphthalene-1,5-disulfonic acid, naphthalene-2-sulfonic acid, nicotinic acid, nitric acid, oleic acid, oxalic acid, palmitic acid, pamoic acid, pyroglutamic acid, salicylic acid, sebacic acid, stearic acid, succinic acid, tartaric acid, thiocyanic acid, undecylenic acid, aminocaproic acid, caprylic acid, alpha lipoic acid, R-lipoic acid, myristic acid, myristoleic acid, palmitoleic acid, elaidic acid, linoleic acid, linolenic acid, linolelaidic acid, arachidonic acid, and a combination thereof.

12. A process for preparing pitolisant or a pharmaceutically acceptable salt thereof, comprising:
a) reacting 3-(piperidin-1-yl)propan-1-ol

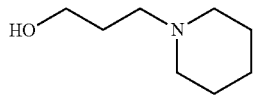

with Formula-(III);

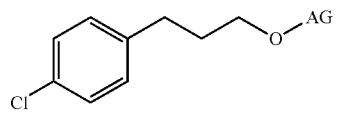

Formula-(III)

in the presence of a solvent and a base to obtain pitolisant, wherein the AG is an activating group;
b) optionally treating pitolisant with an acid to form pitolisant first salt; and
c) converting pitolisant or pitolisant first salt to a pharmaceutically acceptable salt or solid state forms of pitolisant;

wherein the base in step a) is not sodium hydride; and
wherein AG is selected from a methyl sulfonate, an ethylsulfonate, a phenylsulfonate, a tolylsulfonate, a p-nitrophenyl sulfonate, a benzyl sulfonate, a trifluoromethylacyl ester, a trichloromethylacyl ester, a phenylacyl ester, a p-nitro-phenylacyl ester, and a p-chloro-phenylacyl ester.

13. The process of claim 12, wherein the base used in step a) is organic or inorganic base which is selected from sodium hydroxide, sodium carbonate, sodium bicarbonate, sodium methoxide, potassium hydroxide, potassium carbonate, potassium bicarbonate, potassium tertiary-butoxide, triethylamine, t-butylamine, trimethylamine and N, N-diisopropylamine, and a combination thereof.

14. The process of claim 12, wherein the solvent is polar aprotic solvent.

15. The process of claim 12, wherein the solvent of step a) is selected from N,N-dimethylformamide, N,N-dimethylacetamide, dimethylsulfoxide, 1-methyl-2-pyrrolidone, 1-methyl-2-piperidone, 1,3-dimethyl-2-imidazolidinone, acetonitrile, acetone, dichloromethane, ethyl acetate, tetrahydrofuran, acetone, and a combination thereof.

16. The process of claim 12, wherein the step a) reaction is carried out at temperature in the range from about 0° C. to about the reflux temperature of solvent.

17. A process for the preparation of 3-(4-chlorophenyl)-propanol of Formula-(V) comprising:
a) providing 3-(4-chlorophenyl)-propionic acid of Formula-(IV);

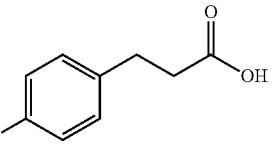

Formula-(IV)

b) converting 3-(4-chlorophenyl)-propionic acid of Formula-(IV) to its acid chloride of Formula-(VI) or acid anhydride of Formula-(VIA);

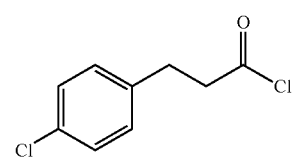

Formula-(VI)

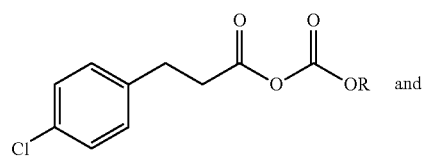

Formula-(VIA)

and c) reducing acid chloride of Formula-(VI) or acid anhydride Formula-(VIA), where R is an alkyl or a phenyl, to obtain 3-(4-chlorophenyl)-propanol of Formula-(V)

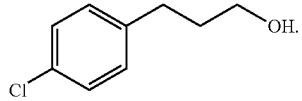

Formula-(V)

18. The process of claim 17, wherein the 3-(4-chlorophenyl)-propionic acid of Formula (IV) in step a) is dissolved in solvent selected from dichloromethane, dichloroethane, tetrahydrofuran, toluene, dioxane, N,N-dimethylformamide, N,N-dimethylacetamide, dimethylsulfoxide, 1-methyl-2-pyrrolidone, 1-methyl-2-piperidone, 1,3-dimethyl-2-imidazolidinone, acetonitrile, acetone, ethyl acetate, methanol, ethanol, isopropanol, n-butanol and combination thereof.

19. The process of claim 17, wherein the conversion of 3-(4-chlorophenyl)-propionic acid of Formula-(IV) to its acid chloride of Formula-(VI) is carried out in presence of a chlorinating agent, including phosgene (C(O)Cl2), diphosgene (Cl3COC(O)Cl), triphosgene (Cl3COC(O)OCCl3), thionyl chloride (S(O)Cl2), oxalyl chloride (ClC(O)—C(O)Cl) and phosphorus oxychloride (P(O)Cl3).

20. The process of claim 17, wherein 3-(4-chlorophenyl)-propionic acid of Formula-(IV) to its acid anhydride of Formula-(VIA) is carried out in presence of a haloformate selected from methylchloroformate, ethylchloroformate, isopropyl chloroformate, isobutyl chloroformate, and phenyl chloroformate.

21. The process of claim 17, wherein the reaction of step b) is carried out in presence of solvent selected from dichloromethane, dichloroethane, tetrahydrofuran, toluene, dioxane, N,N-dimethylformamide, N,N-dimethylacetamide, dimethylsulfoxide, 1-methyl-2-pyrrolidone, 1-methyl-2-piperidone, 1,3-dimethyl-2-imidazolidinone, acetonitrile, acetone, ethyl acetate, methanol, ethanol isopropanol, n-butanol and a combination thereof.

22. The process of claim 17, wherein the reduction reaction of step c) is carried out in presence of a borohydride selected from lithium borohydride, sodium borohydride, potassium borohydride, sodium cyanoborohydride, lithium triethyl borohydride, and a combination thereof, In one aspect, the reduction reaction of step c) is carried out in the presence of sodium borohydride.

23. The process of claim 17, further comprising reacting 3-(4-chlorophenyl)-propanol of Formula-(V) with Formula-(III)

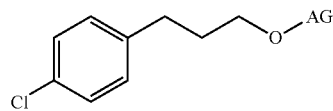

Formula-(III)

to obtain pitolisant;
wherein AG is selected from is selected from a methyl sulfonate, an ethylsulfonate, a phenylsulfonate, a tolylsulfonate, a p-nitrophenyl sulfonate, a benzyl sulfonate, a trifluoromethylacyl ester, a trichloromethylacyl ester, a phenylacyl ester, a p-nitro-phenylacyl ester, and a p-chloro-phenylacyl ester.

24. A process for the preparation of pure pitolisant hydrochloride comprising:
a) providing pitolisant free base;
b) treating pitolisant free base with first salt to obtain pitolisant first salt;
c) optionally treating pitolisant first salt with base to obtain pitolisant free base; and
d) treating pitolisant first salt or pitolisant free base with hydrochloric acid to obtain pure pitolisant hydrochloride.

25. The process of claim 24, wherein the pitolisant first salt is an acid addition salt where the acid is selected from hydrobromic acid, hydroiodic acid, oxalic acid, fumaric acid, maleic acid, succinic acid, acetic acid, adipic acid, ascorbic acid, aspartic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutamic acid, glutaric acid, glycerophosphoric acid, glycolic acid, hippuric acid, isobutyric acid, lactic acid, lactobionic acid, lauric acid, maleic acid, malic acid, malonic acid, mandelic acid, naphthalene-1,5-disulfonic acid, naphthalene-2-sulfonic acid, nicotinic acid, nitric acid, oleic acid, oxalic acid, palmitic acid, pamoic acid, pyroglutamic acid, salicylic acid, sebacic acid, stearic acid, succinic acid, tartaric acid, thiocyanic acid, undecylenic acid, aminocaproic acid, caprylic acid, alpha lipoic acid, R-lipoic acid, myristic acid, myristoleic acid, palmitoleic acid, elaidic acid, linoleic acid, linolenic acid, linolelaidic acid, arachidonic acid, and a combination thereof.

26. The process of claim 24, wherein the base is inorganic or organic base selected from sodium hydroxide, sodium carbonate, sodium bicarbonate, sodium methoxide, potassium hydroxide, potassium carbonate, potassium bicarbonate, potassium tertiary-butoxide, triethylamine, t-butylamine, trimethylamine and N, N-diisopropylamine, and a combination thereof.

27. The process of claim 24, wherein the pitolisant first salt is pitolisant oxalate and pitolisant fumarate.

* * * * *